US010292789B2

(12) United States Patent
Martz et al.

(10) Patent No.: US 10,292,789 B2
(45) Date of Patent: *May 21, 2019

(54) TOOTH POSITIONING APPLIANCE WITH CURVED INTERCONNECTING ELEMENTS

(71) Applicants: Martin G. Martz, Bakersfield, CA (US); Andrew S. Martz, Bakersfield, CA (US)

(72) Inventors: Martin G. Martz, Bakersfield, CA (US); Andrew S. Martz, Bakersfield, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/936,757

(22) Filed: Mar. 27, 2018

(65) Prior Publication Data

US 2018/0214250 A1 Aug. 2, 2018

Related U.S. Application Data

(63) Continuation of application No. 14/566,474, filed on Dec. 10, 2014, now Pat. No. 9,937,018.

(60) Provisional application No. 61/914,832, filed on Dec. 11, 2013.

(51) Int. Cl.
| *A61C 3/00* | (2006.01) |
| *A61C 7/08* | (2006.01) |
| *A61C 7/14* | (2006.01) |
| *A61C 7/22* | (2006.01) |

(52) U.S. Cl.
CPC .............. *A61C 7/08* (2013.01); *A61C 7/14* (2013.01); *A61C 7/22* (2013.01)

(58) Field of Classification Search
CPC .... A61C 7/14; A61C 7/22; A61C 7/08; A61C 7/002; A61C 7/10; A61C 7/12; A61C 7/16

See application file for complete search history.

(56) References Cited

U.S. PATENT DOCUMENTS

| 3,237,305 | A | | 5/1963 | Hegedus | |
|---|---|---|---|---|---|
| 3,593,421 | A | | 7/1971 | Brader | |
| 3,762,050 | A | | 10/1973 | Dal Pont | |
| 3,988,832 | A | | 11/1976 | Wallshein | |
| 4,976,614 | A | | 12/1990 | Tepper | |
| 5,055,039 | A | * | 10/1991 | Abbatte | A61C 7/08 433/24 |
| 5,145,364 | A | | 9/1992 | Martz et al. | |
| 5,310,340 | A | | 5/1994 | Zedda | |
| 6,299,440 | B1 | | 10/2001 | Phan et al. | |
| 6,572,372 | B1 | | 6/2003 | Phan et al. | |
| 7,234,934 | B2 | | 6/2007 | Rosenberg | |
| 8,292,617 | B2 | * | 10/2012 | Brandt | A61C 7/08 433/22 |
| 8,517,726 | B2 | * | 8/2013 | Kakavand | A61C 7/08 433/18 |
| 8,708,697 | B2 | * | 4/2014 | Li | A61C 7/08 433/6 |
| 9,119,691 | B2 | * | 9/2015 | Namiranian | A61C 7/10 |
| 9,795,460 | B2 | * | 10/2017 | Martz | A61C 7/14 |
| 2004/0048222 | A1 | | 3/2004 | Forster et al. | |
| 2004/0067463 | A1 | | 4/2004 | Rosenberg | |

(Continued)

*Primary Examiner* — Nicholas D Lucchesi
(74) *Attorney, Agent, or Firm* — Dorr, Carson & Birney PC

(57) ABSTRACT

A removable, thin-shell tooth positioning appliance having a plurality of tooth-clasping elements for removably engaging attachments bonded onto selected teeth, with flexible curved interconnecting elements connecting the tooth-clasping elements on nearby teeth.

20 Claims, 23 Drawing Sheets

(56) References Cited

U.S. PATENT DOCUMENTS

| | | | |
|---|---|---|---|
| 2004/0170941 A1 | 9/2004 | Phan et al. | |
| 2005/0233276 A1* | 10/2005 | Kopelman | A61C 7/08 433/3 |
| 2006/0068354 A1 | 3/2006 | Jeckel | |
| 2006/0188834 A1 | 8/2006 | Hilliard | |
| 2007/0231765 A1* | 10/2007 | Phan | A61C 7/00 433/6 |
| 2010/0068671 A1* | 3/2010 | Kakavand | A61C 7/08 433/6 |
| 2010/0279245 A1* | 11/2010 | Navarro | A61C 7/08 433/6 |
| 2011/0311937 A1 | 12/2011 | McCance | |
| 2012/0150494 A1 | 6/2012 | Anderson et al. | |
| 2013/0230819 A1* | 9/2013 | Arruda | A61C 7/22 433/6 |
| 2015/0305832 A1* | 10/2015 | Patel | A61C 7/12 433/6 |

\* cited by examiner

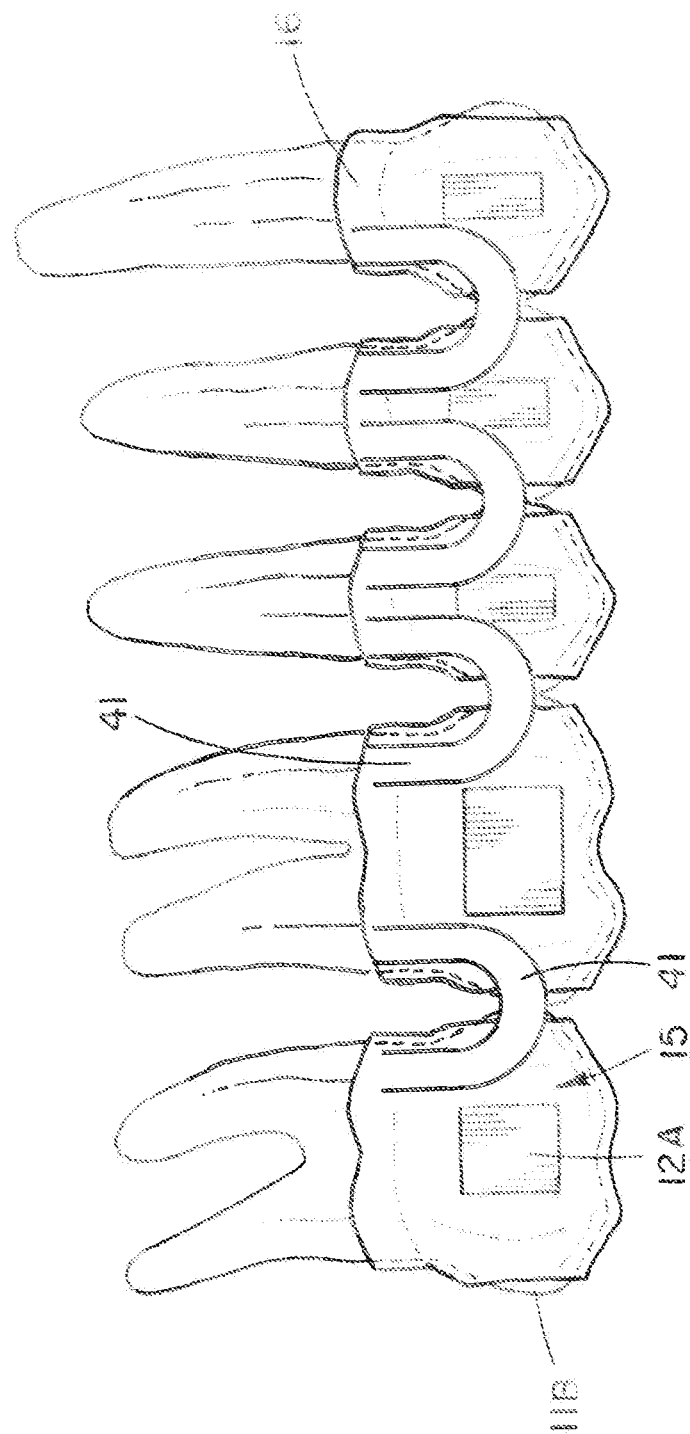

TOOTH POSITIONING APPLIANCE WITH CURVED INTERCONNECTING ELEMENTS

RELATED APPLICATIONS

The present application is a continuation of the Applicants' co-pending U.S. patent application Ser. No. 14/566,474, entitled "Tooth Positioning Appliance With Curved Interconnecting Elements," filed on Dec. 10, 2014, which is based on and claims priority to U.S. Provisional Patent Application 61/914,832, filed on Dec. 11, 2013.

BACKGROUND OF THE INVENTION

Field of the Invention

The present invention relates generally to the field of orthodontics. More specifically, the present invention discloses a tooth positioning appliance with curved interconnecting elements.

Statement of the Problem

A wide variety of orthodontic aligners have been used for many years in repositioning teeth during orthodontic treatment. It should be noted that the terms "aligner", "positioner" and "tooth positioning appliance" are largely synonymous as used in the orthodontic field.

This type of orthodontic treatment typically involves separate tooth positioning appliances for the upper and lower teeth. The tooth positioning appliances fit over the teeth, covering nearly all of the facial and lingual surfaces, and also most of the occlusal, or biting surfaces of the teeth. The early positioners described in the prior art were made from a set of plaster models derived from three-dimensional negative dental impressions of the patient's teeth. The plaster dental models were modified by cutting the teeth apart using a small jeweler's saw or rotary cutting discs and repositioning the plaster teeth in a better, straighter, desired arrangement, and holding the teeth in the new arrangement by using dental wax. The reset teeth molds provide the basis for manufacturing the positioners. The resilience of the material from which the positioner is made provides the energy to move the teeth from their original position toward the new straightened position. From the earliest disclosure of the tooth positioner, many of the proposed designs in the prior art have shown moving the teeth in a series of incremental steps. Making a series of appliances is difficult if the tooth arrangement for each step must be made by hand using plaster and wax.

Starting in the early 1990's, digital technologies have begun to provide orthodontists with fundamentally new tools for delivering orthodontic treatment by fabricating tooth models in small but accurate incremental steps. Commercially-available CAD/CAM software can produce the desired tooth models, from which a progressive series of appliances can be manufactured. These tools include 3D imaging of the patient's dentition, and CAD/CAM (computer-aided design and manufacturing) systems for creating virtual models in orthodontic treatment to then produce customized orthodontic appliances.

An example of the successful orthodontic application of these digital technologies is seen in the commercial service known as the Invisalign® program by Align Technology, Inc. of San Jose, Calif. The Invisalign program is largely based on U.S. Pat. No. 5,975,893 (Chishti et al.) and many related patents, including U.S. Pat. No. 6,398,548 (Muhammad et al.). Invisalign tooth positioners are a progressive series of thin, transparent, U-shaped plastic appliances formed over computer-generated forming patterns grown from a virtual model of the patient's dental anatomy. The process for forming aligners uses a combination of vacuum, pressure and heat. This forming process is informally referred to within the orthodontic laboratory community as the "suck down" process.

In order to produce a series of Invisalign-type tooth aligners, a technician first scans a patient's upper and lower model set to obtain CAD-manipulatable virtual models of a patient's dental anatomy. A model set normally consists of one upper and one lower plaster model of the teeth, palate and gums. Once the virtual model of the original malocclusion has been obtained, a technician will then undertake steps involving extensive manipulation of the virtual malocclusion. This involves extensive repositioning of the teeth according to a comprehensive and sequential procedure, ultimately arriving at a finished or ideal occlusion for that patient. The finished occlusion in the virtual model is consistent with the complete repositioning of the patient's upper and lower occlusion that would result at the end of successful conventional orthodontic treatment.

After the steps described above are accomplished, the technician possesses two versions of the patient's teeth available within the virtual CAD environment. One version represents the original malocclusion and the other represents the ideal occlusion. In other words, the technician has the beginning and the end states.

The next step in the Invisalign process involves the creation of an incremental, progressive series of physical forming models. Each of these forming models represents a snapshot of the patient's future occlusion at specific incremental steps along the patient's proposed treatment sequence between the beginning and the end conditions as described above. To accomplish this, the technician creates a virtual "first transition model" that sees a slight repositioning of all or most of the teeth. This first transition model sees some or all of the teeth being subtly moved from their original pre-treatment positions to a virtual first transition position that is in the direction of their intended finished positions. Similarly, a second virtual transition model is created that sees the virtual teeth being moved again slightly further in the desired directions. The objective of the Invisalign technician is to create a series of progressive models, each biased slightly further than the previous one, and each moving the teeth slightly closer to their finished target positions. A final forming model will take the teeth from the series of transition positions and move them into their final, desired positions.

Once such a series of virtual intermediate forming models has been created and a final forming model has been created by the Invisalign technician, the digital code representing each of the models in the series is directed to operate a computer numerically-controlled (CNC) machine known as a rapid prototyping machine. Within a rapid prototyping machine, the series of physical forming models are grown using any of number of conventional processes, such as stereo lithography or 3D printing. The growing step results in the production of hard, physical duplicates of each of the series of virtual intermediate models and the final model.

The next step of the Invisalign process sees each of the series of physical models being in turn mounted in a suck-down machine where a combination of pressure, heat and vacuum is used to form the actual series of progressive aligners from plastic sheet material of a constant thickness. Once the series of progressive aligners are formed and trimmed, they are sequentially labeled, packaged and shipped to the attending orthodontist. The orthodontist then schedules an appointment for the patient, at which time the aligners and instructions for their use are given to the patient. The patient is instructed to wear the first set of aligners for a period of time, typically two weeks. After that, the first set is discarded and the patient transitions to the next set of the series and so on.

The aligners serve to urge the patient's teeth to move according to the positional biases created virtually by the Invisalign technician. The teeth are progressively biased and urged to move in desired directions toward their predetermined finished positions by the resilience of the polymeric material of the aligner. In response to the gentle but continuous forces delivered by the aligners, certain physiological processes involving the creation and resorbtion of the bone supporting the roots of the teeth are initiated. The net result is the slow, progressive orthodontic movement of the roots of the teeth through the underlying bone toward desirable positions and orientations.

Physiologic processes occur when forces are applied to teeth, resulting in bone resorption and new bone apposition. Studies have shown that the most rapid tooth movement occurs when light gentle continuous forces are applied to teeth. Conventional aligner appliances tend to apply heavier forces when the appliance is first placed on the teeth, and the forces decay away fairly rapidly after the appliance has been in place for a day or so. The reason for making many stages of aligners corresponding to very small incremental movements is to keep the forces lighter, and to re-establish the force when it decays by going on to the next aligner stage. Although in principle the use of many stages of aligners should allow the delivery of lighter more continuous forces, in practice there are still problems with providing adequate tooth engagement and with keeping force delivery within the desired physiological range.

Many conventional removable aligners are limited by their design and the mechanical properties of the clear thermoplastic materials that are currently utilized. The clear polymeric materials make the aligner nearly invisible, and that is a great advantage over fixed stainless steel hardware and metal braces. On the other hand, conventional polymeric materials used in forming aligners have a very limited ability to flex. This is particularly a problem when aligning teeth that are not fairly well lined up in the beginning of treatment.

Even when very small movements during each stage are attempted, the appliance may fail to properly engage teeth that need to be moved because the appliance is not adequately flexible and is not designed to allow movement within the plane of the material. If a particular aligner fails to properly engage a tooth, then that tooth will not move to the proper place to engage the next successive aligner in the series. The only present solutions available when aligners fail to properly engage a tooth are: (1) reduce the amount of movement attempted for that particular stage; or (2) place a larger bonded attachment on the tooth. Both of these solutions require reworking the computerized treatment plan. If the plan is not revised, with each successive stage of the appliance, the fit of the aligners deteriorates, and after just a few stages, it becomes obvious that the teeth are not moving according to the original computerized treatment plan, forcing a revision of the treatment plan.

Solution to the Problem

The present invention seeks to overcome the limitations of the lack of flexibility of the appliance material by providing a tooth-clasping element for each tooth that is connected by curved interconnecting elements to the tooth-clasping elements of nearby teeth. The curved interconnecting elements are flexible enough to allow each tooth-clasping element to remain firmly engaged in place. The flexible properties of the interconnecting elements are controlled by the choice of materials, by the cross-section of the interconnecting elements, and by the shape of the interconnecting elements. The shape chosen in most of the embodiments of the interconnecting element in the present invention is a small radius loop configuration, where the radius of the loop is preferably about half of the width of the tooth.

SUMMARY OF THE INVENTION

This invention provides a removable, thin-shell tooth positioning appliance having a plurality of tooth-clasping elements for removably engaging attachments bonded onto selected teeth, with flexible curved interconnecting elements connecting the tooth-clasping elements on nearby teeth.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 6 illustrates an initial view of unmoved tooth, with CR and CC points located. FIG. 7 shows lingual root tipping movement with crown center remaining stationary. FIG. 8 shows a buccal crown tipping movement with center of resistance remaining stationary. FIG. 9 indicates horizontal transverse translational (bodily) movement without tipping.

FIG. 22 shows another embodiment of the appliance fitted on teeth in the upper right quadrant, similar to the view shown in FIG. 12. In this embodiment the large curved loops of the interconnecting elements 41 are folded over so they are in an inverted position. In this position they still function in much the same way, but they are less likely to interfere with buccal frenum attachments. The mechanics of the inverted loop tend to keep the root positions closer together as the loop is stretched open. It should be noted that the entire appliance, including the interconnecting elements 41, can still be fabricated as a single piece.

DETAILED DESCRIPTION OF THE INVENTION

Figures 1, 2:
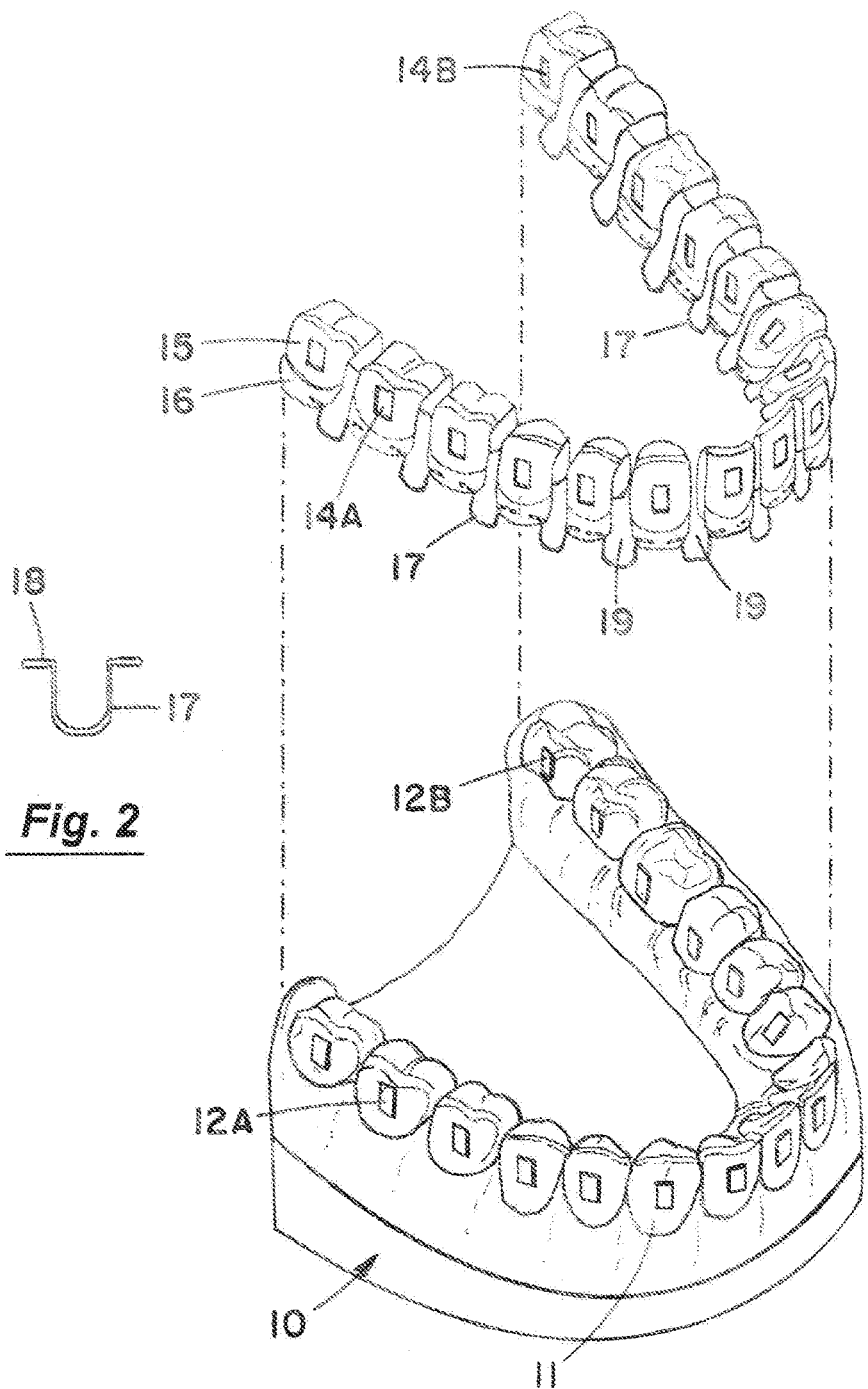
FIG. 1 is a perspective view of a lower dental arch 10 with the present appliance positioned above it. The U-shaped wire interconnecting elements 17 are shown on both buccal and lingual sides of the teeth 11. Dotted lines indicate the path the appliance would follow to be seated in place on the teeth 11.
FIG. 2 is a front elevational view of an interconnecting element 17 having flattened ends 18.

Turning to FIG. 1, the present tooth positioning appliance includes the following major elements: (1) bonded attachments 12A, 12B bonded to the lingual or buccal surfaces of selected teeth 11; (2) tooth-clasping elements 15 removably engaging the bonded attachments 12A, 12B; and (3) curved interconnecting elements 17 extending between adjacent tooth-clasping elements 15. In particular, the tooth-clasping elements 15 include recesses designed to fit over projecting elements or buttons called "bonded attachments" 12A, 12B that are bonded directly to the teeth. The bonded attachments 12A, 12B are not typically removable by the patient during the course of active orthodontic treatment.

It is desirable to have the tooth-clasping elements 15 on the front teeth made of a clear polymeric material. Currently, several different plastic materials including urethanes and polycarbonates can be thermoformed over tooth models to produce the desired tooth alignment appliances. The material can be any suitable material. It should also be noted that the tooth-clasping element 15 can be a separately manufactured part or a functional region of a single-piece appliance.

Figure 5:
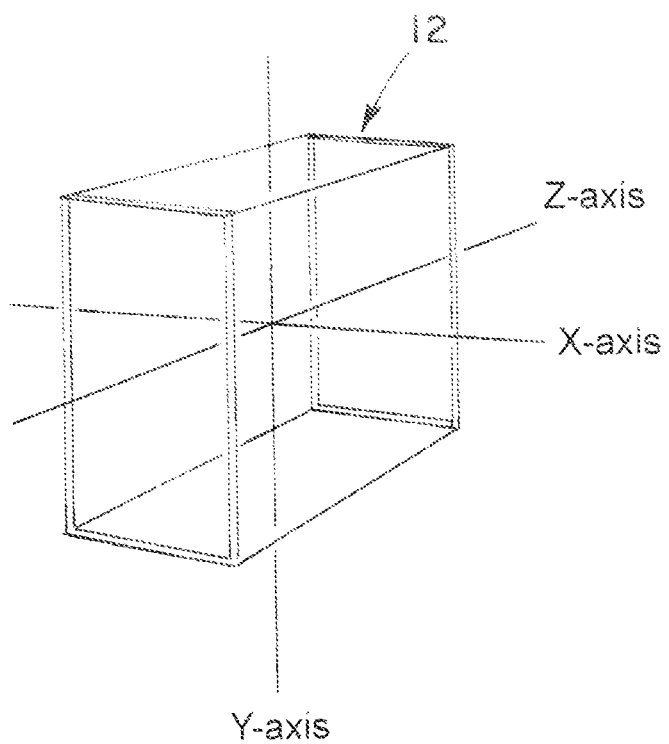
FIG. 5 shows a 3-dimensional view of a rectangular bonded attachment 12A with the X, Y, and Z axes indicated.

The bonded attachments 12A, 12B are typically bonded to the buccal or lingual surfaces of selected teeth 11, as shown in FIG. 1. For example, the bonded attachments can have a substantially rectangular shape with parallel sides, as shown in FIG. 5, although it is to be understood that there are many possible shapes for bonded attachments that would be suitable. The bonded attachments 12A, 12B are utilized for two purposes: (1) the bonded attachments 12A, 12B increase the retention of the tooth-clasping elements 15 to the teeth 11, (or in other words, the appliance is less likely to become dislodged from the desired location on the teeth); and (2) the bonded attachments 12A, 12B have a shape that allows the tooth-clasping elements 15 to transmit desired forces to the teeth in three-dimensions, thereby providing control over root movement. In the rectangular bonded attachment 12A shown in FIG. 5, the parallel outer edges of the attachment 12A provide surfaces for positive engagement to allow forces to be applied to the teeth to accomplish root movement under control. Inner surfaces of an attached projection such as can be provided by grooves or special shapes can also provide this control. Grooves or special outside shaping can help guide the tooth-clasping element into position. The bonded attachments can be pre-made of any suitable material including dental composite, clear or tooth-colored ceramic materials, or any suitable clear plastic material. The attachments 12A can be bonded to the teeth using conventional bonding techniques and adhesives that are well-known in the art including the steps of mildly acid-etching the enamel prior to bracket placement. A technique well known in the art called indirect bonding can be utilized, with a pre-formed guide made of flexible material holding the attachments in the desired position while the adhesive is curing to ensure accurate attachment placement on the teeth. The bonded attachments can alternatively be fabricated out of dental composite using pre-made hand-held molds for one tooth at a time placement, commercially available for this purpose. A third alternative is to utilize a mold made using 3D CAD/CAM technology, where the shape and the size of the bonded attachments are planned in the computer and a model of the entire dental arch with attachments in place is printed using a 3-D printer. From this model, a mold is made from which to fabricate and place dental composite attachments in precisely the right location directly on the teeth.

Preferably, the tooth-clasping elements 15 include a hole of precise dimensions (e.g., a rectangular hole) through which the bonded attachment 12A, 12B projects to removably engage the tooth-clasping element 15. Alternatively, a recess on the inside of the tooth-clasping element 15 of exactly the same shape and size as the bonded attachment 12A, 12B should work equally as well, particularly if the tooth-clasping element 15 is printed, because of the ability of the printing process to produce a more precise fit than can be obtained by thermoforming.

The tooth-clasping elements 15 are be attached to flexible curved interconnecting elements 17 of many types, as illustrated in the drawings. In some embodiments of the present invention, the appliances are made of one piece of material, and the tooth-clasping element and the flexible interconnecting elements are all part of a monolithic whole unit. Functionally, different regions of the single-piece positioner serve as the tooth-clasping element 15 and the flexible interconnecting elements 17.

It is anticipated that the improved tooth positioners of the present invention will be produced by planning and designing the appliances using computerized 3-D CAD/CAM software. Many off-the-shelf software programs are currently available that are capable of this function. Over the long-term, it will be beneficial to write new software that integrates easily with the skill levels of orthodontist end-users, to simplify their use of the product. Open-source software that can be modified is currently available to perform this function. The standard surface mapping computer algorithms define the surface as a series of triangles. The actual physical production of the appliances can be accomplished by vacuum-forming thermoplastic materials over models produced digitally and combining the thermoformed portion of the appliance with the other necessary elements. This step is followed by using computer automated trimming technologies such as CNC milling or laser cutting. In particular, the clear tooth-clasping elements could be produced by vacuum thermoforming. In the single-piece embodiments of the present invention, the tooth-clasping elements and the flexible interconnecting elements could all be vacuum thermoformed together.

Alternatively, positioners can be made without first producing 3D models via 3D printing. A big advantage of direct 3D printing is that more complex shapes could be more easily printed, and almost no trimming of excess material would be necessary, saving time and avoiding wasted material. Some new 3D printers can print more than one material at the same time. The flexible interconnecting elements could be printed along with the tooth-clasping portion, and they could be made of differing materials. The materials can be blended or intertwined which will avoid the need for a separate attachment step in manufacturing. Another option involves direct CNC milling of the appliances or portions of the appliances from a block of plastic material. It is anticipated that the present appliances will be made in a series. Each appliance will move teeth a small distance, and then successive stages will continue the movement in small steps toward the desired goal. Each stage of the appliance can be fabricated in such a way as to fit over the teeth where they ideally should be for the next step or stage. The appliance will have to be deformed to fit over the teeth in their present position. The tooth-clasping elements 15 should fully engage each tooth. If the patient wears the appliance for a sufficient number of hours each day, after the appliance has been worn for a few weeks, the resiliency of the appliance will carry the teeth toward the desired position for the end of that particular stage. Then the next stage of the appliance will be placed on the teeth and will carry the teeth another prescribed distance, and so on until the desired final position is reached. It is likely to be necessary to take new impressions or new digital scans every few stages to keep the appliances fitting accurately as the process of straightening the teeth progresses.

Many of the accompanying drawings show tooth-clasping elements fitted over individual teeth. If adjacent teeth are aligned, and it is anticipated that this will routinely occur during later stages of treatment, it is not necessary to generate a separate tooth clasp for each individual tooth in each stage. Groups of adjacent teeth may have tooth-clasping portions combined if these teeth are well aligned with each other. It may also be desirable in certain stages of treatment to combine teeth together in groups to be used as anchorage units, to provide better control over the movements of other groups of teeth. In these cases, the present appliance can be divided into multiple thin-shell segments. Each thin-shell segment can be designed to engage a group of adjacent teeth (i.e., one or more adjacent teeth). However, only select teeth in each group are equipped with bonded attachments 12A, 12B to engage corresponding tooth-clasping elements in the thin-shelled segment. This concept is somewhat similar to that used in orthodontic treatment with fixed braces, especially when extraction spaces are being closed and is well-described in the prior art. It is also possible to combine features of several of the embodiments described in this disclosure into one appliance to accomplish certain types of movements more efficiently.

To summarize, the embodiment of the present invention shown in FIGS. 1-4 includes clear tooth-clasping elements 15 fitted over teeth 11 to which bonded attachments 12A, 12B have been placed on both the buccal and lingual sides. The tooth-clasping elements 15 are connected together using flexible U-shaped interconnecting elements 17 made of wire loops attached to the flange (or extension) 16 of the tooth-clasping element 15 that covers part of the gum tissue adjacent to the teeth on both the buccal and lingual sides. FIG. 2 is a front elevational view of a wire interconnecting element 17 having flattened ends 18. The wire can be made preferably of nickel-titanium shape-memory wire, heat treated to the desired shape and of the appropriate dimensions, although other suitable materials can be utilized. The clear tooth-clasping elements 15 will be nearly invisible on the teeth 11, and the wire interconnecting elements 17 will go over the gum tissue in a less visible zone. This embodiment may have the greatest flexibility, and it is therefore anticipated this will be used to correct tooth rotations and crowding in situations where other embodiments cannot be used. This embodiment may be somewhat more difficult to manufacture because of the multiple parts and materials. The curved interconnecting elements 17 can also be mounted in an inverted position. Although the loops will be in a more visible location, inverted loops may be preferred for posterior teeth.

In particular, the bonded attachments 12A, 12B are preferably placed on the buccal and lingual aspects of all teeth, upper and lower, although there may be some instances where not all teeth have all the attachments. In the illustrations, rectangular bonded attachments are shown. The tooth-clasping elements 15 are preferably made of a clear plastic material or other suitable material cover most of the facial, occlusal, and lingual surfaces. The tooth-clasping elements adapt tightly to and conform to the outer contours of the teeth and the bonded attachments. There can optionally be an open window through which the bonded attachment 12A, 12B projects, or the bonded attachment can be covered completely by the appliance. Either way, the tooth-clasping element 15 adapts tightly to the bonded attachment 12A, 12B and the portion of the crown of the tooth covered by the tooth-clasping element so as to allow forces transmitted to the tooth-clasping element 15 to be directly transmitted to the tooth. The forces can be in any direction needed to correct the malocclusion. The curved interconnecting elements 17 are preferably made of wire with flattened ends to prevent the wire from being pulled out of the material covering it that forms the bond of the wire with the tooth-clasping element 15.

This embodiment of the present invention includes a removable orthodontic appliance that will be worn by an orthodontic patient after the bonded attachments 12A, 12B have been placed on the teeth by the orthodontist, preferably using a method that allows great precision such as the aforementioned indirect bonding method or a computer-generated mold. The appliance will be made in multiple stages, each one moving the teeth in small increments toward a final desired goal envisioned by the orthodontist and planned in the computer using commercially-available CAD/CAM software designed for this purpose. This embodiment is most likely to be used in the early stages of treatment when the teeth are in their most crowded or irregular state. The flexibility of Ni—Ti wires is greater than the flexibility of any of the other materials utilized on the interconnecting elements in other embodiments disclosed herein. Therefore, this should allow complete engagement of the tooth-clasping elements in more complex orthodontic cases than have previously been treatable with removable positioner appliances.

The present appliance may be formed from a model of the patient's dental anatomy made of conventional plaster or a dental stone model, made by pouring the plaster or dental stone when it is uncured (wet) into an impression made of alginate, polyvinyl siloxane, silicone, polysulfide rubber or other suitable dental impression material. After the plaster or stone has cured (dried), the excess material is trimmed using a conventional rotating wheel model trimmer so the base is flat and the edges of the base are smooth. Alternatively, the dental model can be obtained by using conventional digital scanning techniques of the teeth directly in the mouth using a commercially-available digital intra-oral scanner, or the plaster or stone model can be scanned using a commercially available digital model scanner, or the impression itself can be scanned using a digital scanner or a computerized tomography scanner (CT). From the digital data obtained by the scan, a three-dimensional model can be produced using a commercially available stereo lithographic printer, or a commercially-available rapid prototyping printer, or a model can be produced using a commercially-available CNC milling machine operating on any suitable material, most likely a plastic block.

The three-dimensional images of the teeth (anatomic portion) are attached to the base of the dental model. The images of the teeth (virtual teeth) are the same size and shape and in the same relative location to each other as the real teeth in the mouth of the dental patient. In other words, the model of the teeth is an accurate representation of the real teeth in the mouth of the patient.

The bonded attachments 12A, 12B serve the purpose of providing an altered shape attached to, but different from the surface of the tooth. The bonded attachments are vital for retention of the removable appliance in the correct location on each tooth. The bonded attachments also allow the tooth-clasping element to transmit forces to the tooth so as to provide complete control over the position of the tooth in three dimensions. The bonded attachments protrude from the surfaces of the teeth, and in this particular illustration, the attachments have straight sides to properly orient the tooth-clasping elements in a desired position. As a general rule, the bonded attachments will be placed on the teeth prior to beginning any tooth movement.

The tooth-clasping elements 15 are formed utilizing an accurate model of the teeth 11. As shown in FIG. 1, there are separate tooth-clasping elements 15 to fit over each tooth in the arch, with shapes corresponding to the shape of each tooth. It can be seen that there are spaces between each tooth-clasping element (even if the teeth themselves are touching). The inner surface of the tooth-clasping element should be almost exactly the same shape and dimensions as the outer surface of the tooth to which it will be applied. Because the material from which the tooth-clasping element 15 is made has some thickness, the outer surface of the tooth-clasping element 15 will have greater dimensions but a similar shape corresponding to the inner surface of the tooth-clasping element. The outer surface is essentially a slightly enlarged or inflated version of the inner surface. The tooth-clasping element 15 typically has components that touch the tooth 11 on the buccal (outer), occlusal (top of bottom teeth, and bottom of top teeth) and lingual (inner) surfaces.

The tooth-clasping element 15 may also include a clear flange (or extension) 16 as an integral part of the tooth-clasping element 15. The flange 16 generally extends over the gum tissue of the patient on the facial and lingual sides of each tooth by a distance of approximately 2 to 3 mm, although the flange does not have to project that far. The flange 16 does not typically contact the gum tissue. There is clearance of at least 0.5 to 1 mm.

The flange 16 can serve as the attachment area for the flexible curved interconnecting elements 17. It is also possible to attach the flexible interconnecting element 17 directly to the main body of the tooth-clasping element 15, for example in the area between the bonded attachment 12A, 12B and the gum line without utilizing the flange. This may be particularly desirable on posterior teeth where the need to hide the loop behind the lips would not be as much of a cosmetic concern. The advantage this would provide is to reduce the risk of interference between the loops and the buccal frenum attachments. There would be a smaller vertical dimension to the appliance with the same sized loops.

In this particular embodiment, each interconnecting element 17 is a U-shaped wire, preferably made of heat-treated Ni—Ti shape memory wire. The U-shaped interconnecting element 17 extends outward slightly to avoid contact with the gum tissue, and maintains an open space 19 between adjacent tooth-clasping elements and allows range of movement. The exact dimensions of the U-shaped loop, and the thickness and heat-treatment of the wire to achieve the desired shape-memory properties can be varied to produce the desired physiologic forces applied to the tooth-clasping elements, and therefore the desired forces applied to the teeth. Alternatively, the flexible interconnecting element could be made of any suitable material. In this particular embodiment, the attachment means of the interconnecting element 17 to the tooth-clasping portion is not shown, primarily because it is transparent, and therefore would not be readily visible.

It should be noted that the interconnecting elements 17 have flattened ends 18 in the embodiment shown in FIGS. 1 and 2. If the flexible interconnecting element 17 is made of wire, the end of the wire is bent approximately 90 degrees and is placed in a hydraulic press to flatten the end 18, possibly with some small serrations pressed into the metal wire. The bent ends prevent the wire from being pulled out of the clear plastic that encases them. There are several conventional methods by which the interconnecting element could be attached to the flange of the tooth-clasping element. (1) Clear cold-cure acrylic could be applied over the wire in much the same way that wire elements are attached to the plastic of retainers commonly used in orthodontics today. (2) The same plastic material from which the tooth-clasping element is made could be applied in a molten state using a glue-gun nozzle and could cover the wire with a thin layer. This technique could be automated, and the nozzle could be robotically controlled on an assembly line. (3) A small plastic panel of approximately the same size as the flange of the tooth-clasping element could be placed over the flexible interconnecting element ends, and while being held in place, a focused ultrasonic welder waveguide horn could be placed adjacent to the two pieces of plastic to fuse the flange and the small panel together.

Alternatively, rather than flattening the ends of the wire segments, other means could be employed to prevent the wire from pulling out of the plastic, such as a zigzag in the wire, or bending the wire into an L-shape, or doubling it back on itself to form a T-shape, or forming the wire into a small circle, etc.

It should be noted that larger segments of wire could be used than the short segments shown in FIGS. 1 and 2. A longer segment of wire, containing multiple loops could be used to connect multiple tooth-clasping elements together. The wire could be attached using various means, including: (1) direct cementation using a composite or plastic cement, covering the wire; or (2) the tooth clasping elements could be printed or formed in such a way as to have a groove or recess to receive the wire, and the wire could even snap into place if the groove is designed so that the opening to receive the wire is slightly smaller than the wire and the portion of the groove where the wire is intended to reside. The groove can be square or rectangular in cross-section to receive a wire which is square or rectangular in cross-section. The wire could even be one piece with multiple loops in it.

Figure 3:
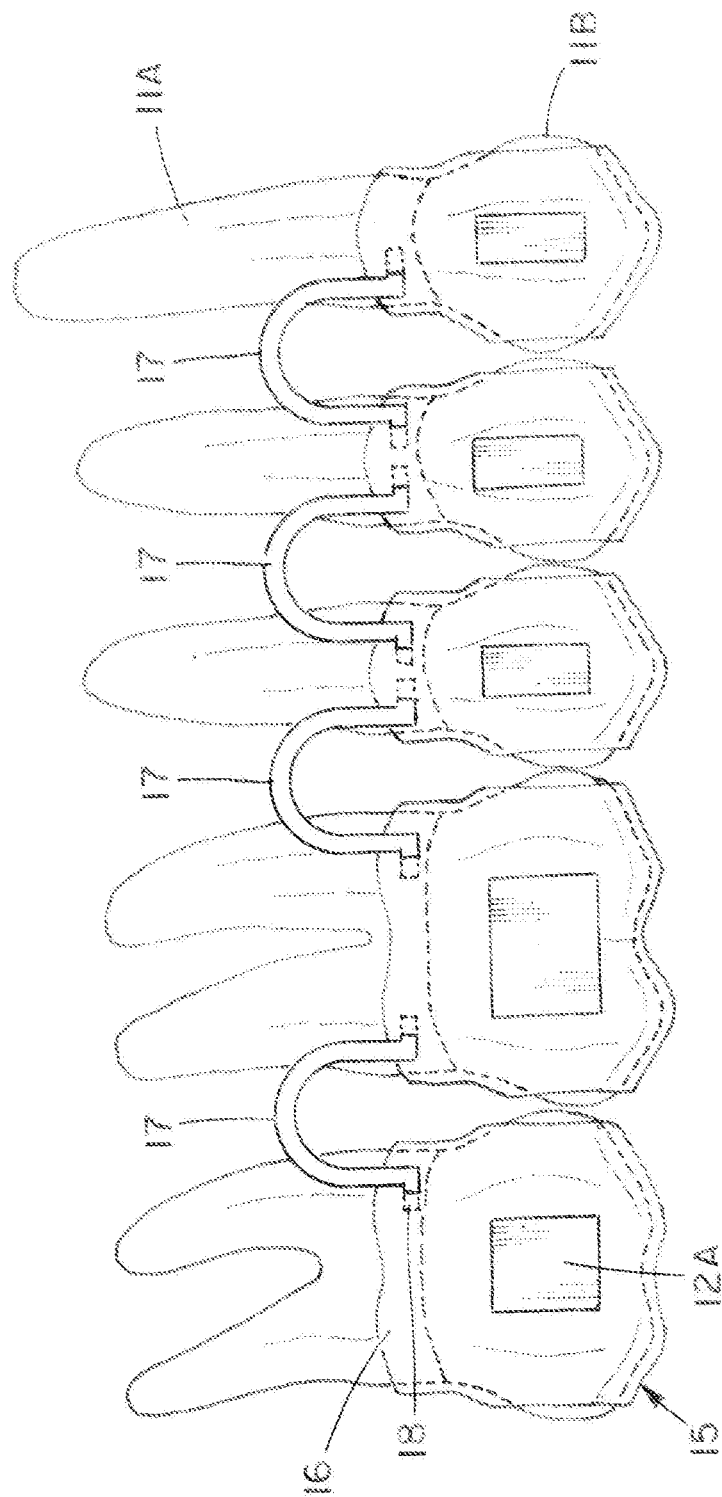
FIG. 3 is a side view of a portion of the appliance fitted on some of the teeth in the upper right quadrant.
Figure 4:
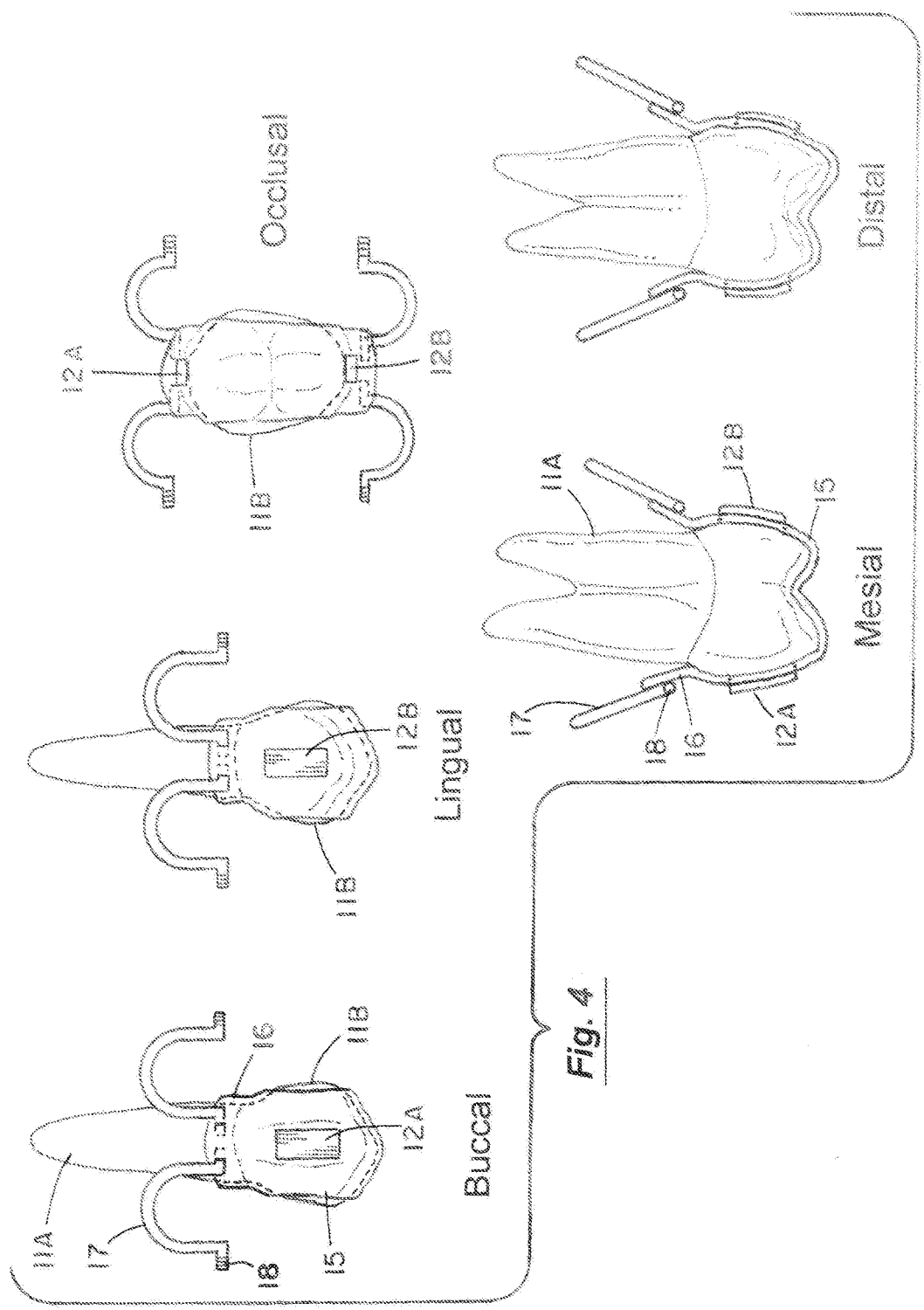
FIG. 4 shows views from five different directions of a single tooth (upper right first premolar) with bonded attachments 12A and 12B, a tooth-clasping element 15, and U-shaped wire-loop interconnecting elements 17 in place.

FIG. 3 shows a right side view of some of the upper teeth with a portion of the same type of removable appliance shown in FIG. 1 installed on these teeth. Reference number 11A designates the root of the upper right cuspid tooth. The mesial surface 11B of the crown of the upper right cuspid tooth can be seen just sticking out beyond the mesial edge of the tooth-clasping element. FIG. 4 shows views from five different directions of a single tooth (upper right first pre-molar) with bonded attachments 12A and 12B, a tooth-clasping element 15, and U-shaped wire-loop interconnecting elements 17 in place.

Note the size of the bonded attachments 12A varies with the size of the teeth. The bonded attachments in this view protrude through holes in the clear tooth-clasping elements. The holes are of the same size and shape as the bonded attachments. As discussed earlier, it is not necessary to use rectangular bonded attachments, nor is it necessary to use holes in the tooth-clasping elements to allow protrusion of the bonded attachments through the tooth-clasping elements. A simple recess in the inner surface of the tooth-clasping element precisely corresponding to the size and shape of the chosen bonded attachment geometry will still provide the necessary clasp function that is vital to the proper functioning of this appliance. Note there are spaces 19 between each of the tooth-clasping elements 15 even though the teeth themselves may be in contact. The space prevents the tooth-clasping elements from interfering with each other. FIG. 4 provides an upper right first premolar tooth viewed from five different angles showing a single tooth-clasping element 15 with interconnecting elements 17 attached as they would be positioned to reach toward adjacent teeth.

FIG. 5 shows a perspective view of a bonded attachment 12A, with the three axes of tooth movement intersecting within the center of the crown of the tooth (not shown) on which the bonded attachment is fixedly mounted. The x-axis in this case is a horizontal axis in the anterior-posterior direction. The y-axis is a vertical axis. The z-axis is a horizontal axis in the transverse direction. The bonded attachment can be positioned away from the center of the crown of the tooth. When forces act on the bonded attachment, depending on the direction of the force, the force produces a moment, which may cause a more complex movement of the tooth than is at first anticipated.

Figure 6:
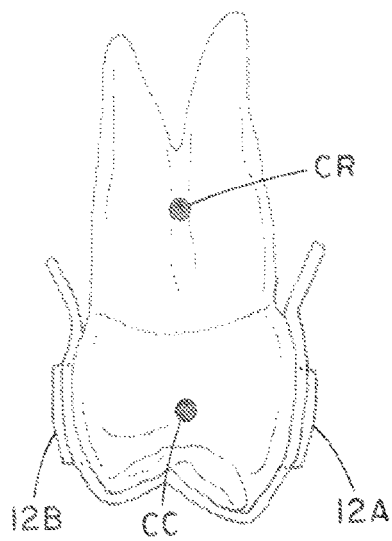
FIGS. 6-9 provide views of three types of simple tooth movement in the transverse plane.
Figure 7:
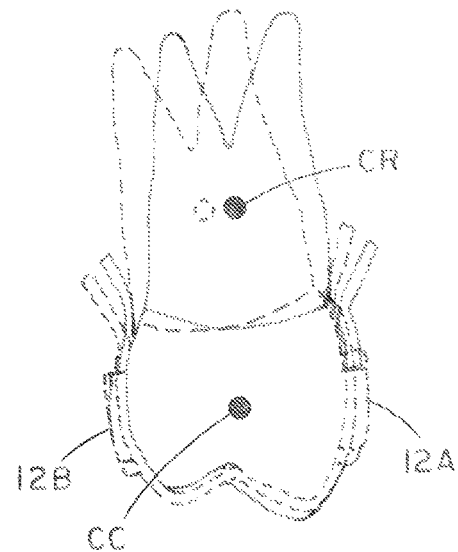

FIGS. 6-9 illustrate three different transverse movements, along the z-axis, as shown in FIG. 5 (i.e., not in the X-Y planes of the bonded attachments.) An upper right first premolar tooth is shown in all the drawings, viewed on the distal side. All of these movements require the resetting of teeth from the original position to a new desired position, either in a digital 3-dimensional file representing the positions of teeth, or using a dental model, whether resetting teeth manually, or when generating 3-D models from computerized digital files. FIG. 6 provides a reference view. FIG. 7 shows lingual transverse movement of the root with the center of the crown (CC) staying in the original position. The movement is a root tipping movement that is relatively difficult to accomplish, even when using fixed braces. For this movement, it would be desirable to use a trans-palatal bar to provide additional support to assure the desired movement. The movement is accomplished primarily by vertically moving the buccal and lingual sides of the teeth with the bonded attachments, although it can be seen that there are small transverse movements of the tooth surface taking place along with the bonded attachments.

Figure 8:
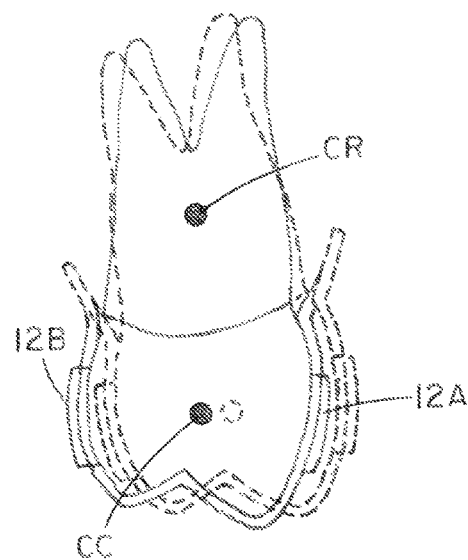

FIG. 8 shows buccal transverse movement of the crown with the center of the root (or center of resistance, CR, to movement of the tooth) staying in the original position. This tipping movement of the crowns of the teeth is relatively easy to accomplish, because the roots of the teeth naturally tend to remain in place. The movement is accomplished by a combination of movements of the buccal and lingual surfaces of the teeth along with the bonded attachments. In this drawing, it can be seen that there is approximately the same amount of vertical and transverse movement of the bonded attachments taking place, although the transverse tipping movements of the crown tend to naturally occur when opposing vertical forces are applied to the crowns of teeth, because of the resistance of the bone surrounding the roots.

Figure 9:
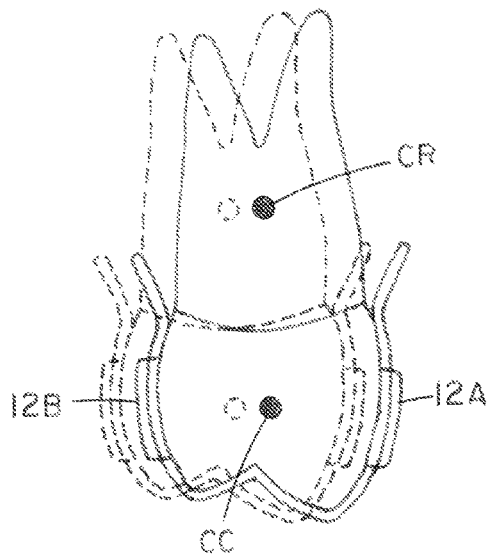

FIG. 9 shows buccal or lingual transverse movement of the entire tooth, with the center of resistance (CR) and the center of the crown (CC) moving exactly the same distance and in the same direction. There is no tipping of the tooth taking place. This type of movement requires bonded attachments, with very good engagement of the tooth-clasping element with the flat top and bottom surfaces of the bonded attachments to prevent the tooth from tipping.

Figure 10:
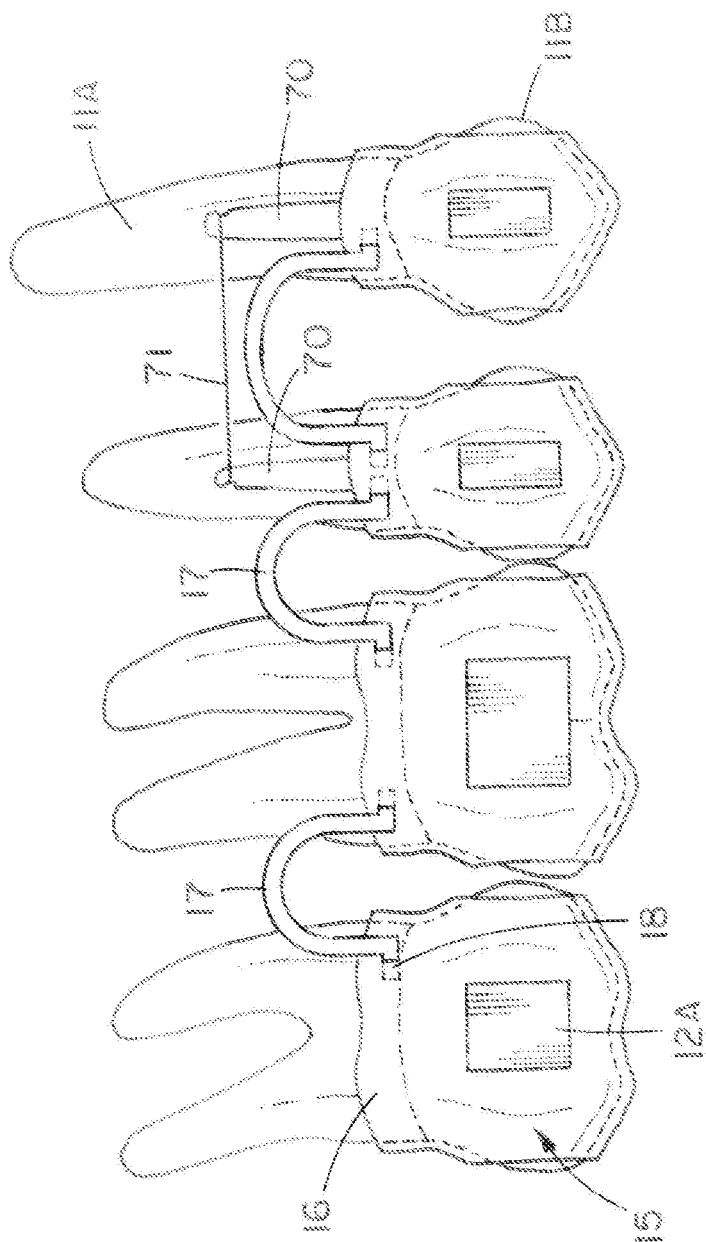
FIG. 10 is a side view of an appliance fitted on some of the teeth in the upper right quadrant. The appliance is similar to that shown in FIG. 3, but a tooth has been extracted and other teeth are being moved to close the extraction space. The tooth-clasping element of the teeth adjacent to the extraction space on either side has been modified to include a straight arm extension of the buccal flange. The arm extends over the gum line and includes a hook, or button, or other attachment means for installing an elastic band to apply additional force to close the space. Because the elastic band is attached near the center of resistance of the tooth near the center of the root of the tooth, the tipping moment is reduced, thereby making it easier to avoid tipping the tooth while the space is closing.

FIG. 10 shows an embodiment of the present invention that includes a localized extension of the flange 16 of the tooth-clasping element 15 on selected teeth to produce what is essentially an arm 70 for the attachment of stretchable elastic members 71 (e.g., rubber elastic bands, made of any suitable material). For instance, if a tooth has been extracted as part of the orthodontic treatment plan, the closure of the space while keeping the tooth roots parallel on either side of the extraction space (avoiding tipping the crowns of the teeth into the extraction site) has typically been a severe problem when using removable orthodontic appliances in the past. This is also a problem with fixed braces on teeth. One of the solutions routinely used with fixed braces is to place a rigid arm with a retentive hook on the brackets (an element commonly used with fixed braces) on either side of the extraction space to allow the use of elastic bands to help close the space. The center of resistance for each tooth is located approximately in the center of the root of the tooth. Placing the attachment point for the elastic band very close to the center of resistance of the tooth reduces the tipping moment as the force from the elastic is applied. The roots tend to stay more parallel when this method is used to close the space. In the same way, the flange 16 of the tooth-clasping element 15 can be extended to a point close to the center of resistance of the tooth, and an elastic band 71 can be utilized in the same way. If there are arms on both the buccal and lingual side of the teeth, the forces would be parallel, and the rotational moment present with a band 71 only on the buccal side would be cancelled. As a practical matter, it would be uncomfortable for the dental patient with a long appliance arm covering the gum tissue on the lingual side of the teeth to wear such a rubber band, although perhaps not impossible under certain circumstances. It depends on the curvature of the palatal tissue. Another possible use might be where root movement is desired, such as to upright a tipped tooth, but where there is no interdental space. To avoid tipping teeth that we do not want to tip, a group of teeth could serve as the anchor.

Figure 11:
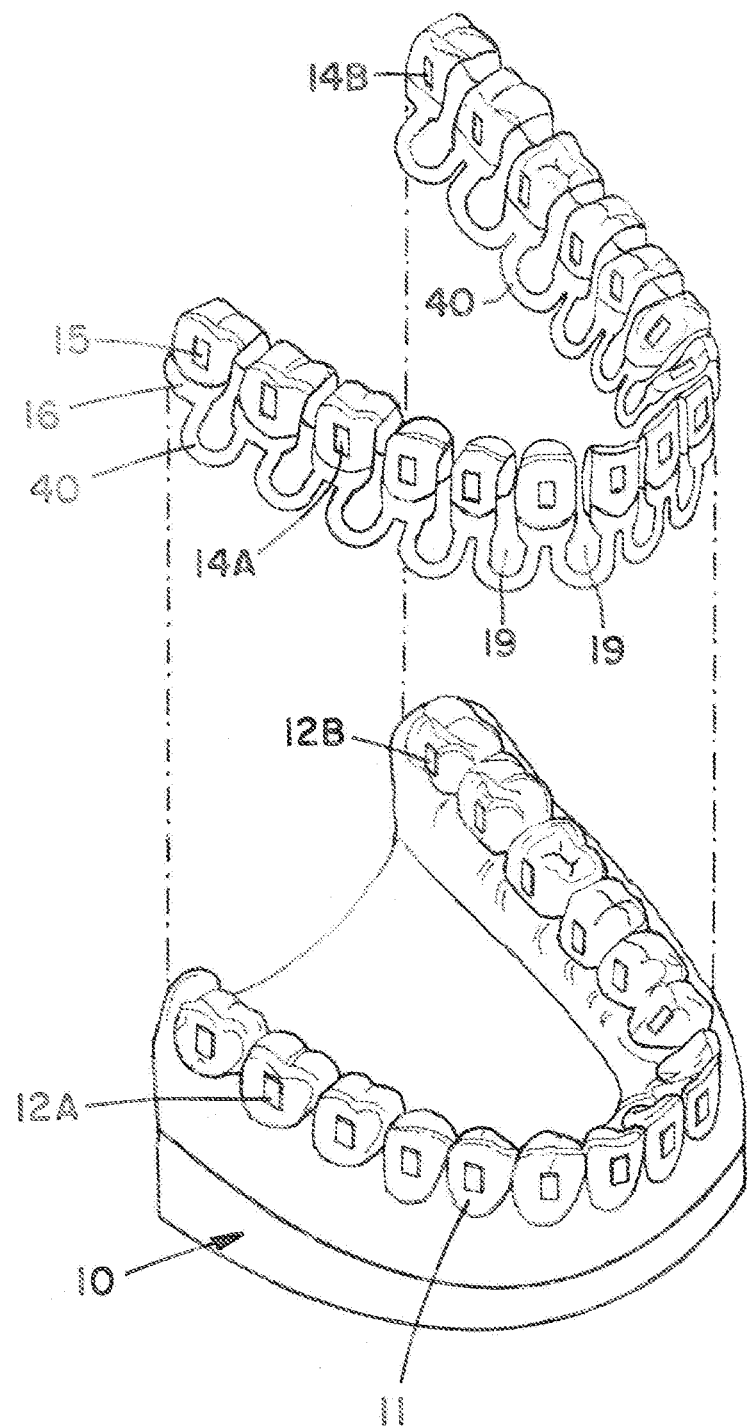
FIG. 11 shows a perspective view of a lower arch dental model with another embodiment of the appliance positioned above it. The appliance is made of a single piece of material, but localized regions of the appliance function as tooth-clasping elements and as flexible curved interconnecting elements. Dotted lines indicate the path the appliance would follow to be seated in place on the model.
Figure 12:
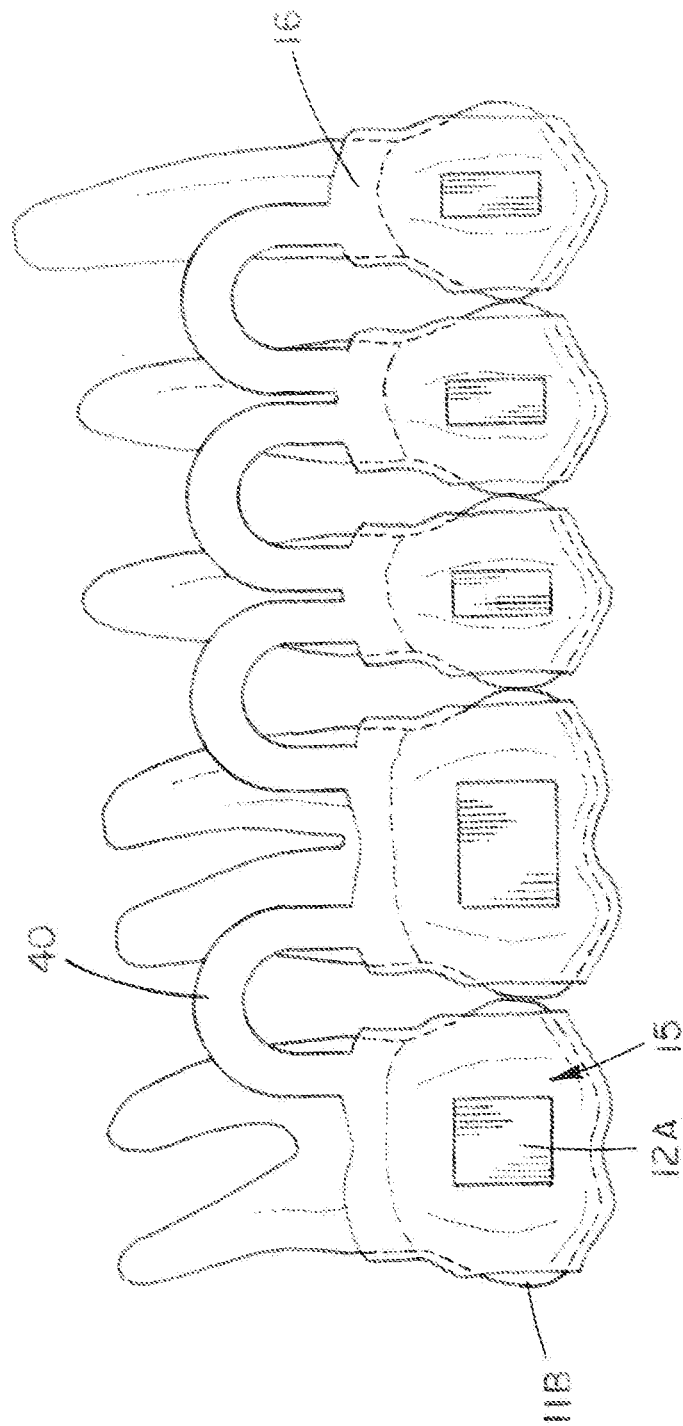
FIG. 12 shows a side view of a portion of the appliance in FIG. 11 fitted on some of the teeth in the upper right quadrant.

FIGS. 11 and 12 show an embodiment formed from a single piece of clear vacuum-formed or printed material. Functionally, the flexible plastic interconnecting elements 40 may not have the flexibility of wire interconnecting elements, but they will be far easier to manufacture if the appliance is printed, and the loops will be less visible. It is anticipated that the flexibility of the clear plastic curved interconnecting elements will be sufficient to make the appliance workable without resorting to the complex manufacturing and assembly process required to utilize wire loops as in the first embodiment. If the appliance is thermoformed and then cut, the instruction set for computerized mill cutting or laser cutting will be complex.

This embodiment utilizes the same bonded attachments 12A, 12B as the other embodiments. The removable positioning appliance is in two pieces, upper and lower. Each arch appliance is fabricated as a single piece appliance with regions that function as tooth-clasping elements 15 and curved, flexible interconnecting elements 40. The regions of the appliance that engage the teeth and function as tooth-clasping elements are almost identical in size shape and form to those of the previous embodiments. The regions 40 of the appliance that serve the function of the flexible interconnecting elements are curved, and are approximately the same overall size as the U-shaped wire connecting elements of the first embodiment. Functionally it is almost identical to the first embodiment, except the plastic loop is not as flexible or as strong as a wire loop. This embodiment can be made as a thermoformed appliance over a series of tooth models, much like currently-marketed aligners, but trimming away the excess material may be more difficult. It can be accomplished using a CNC milling cutter, or a laser cutter, but will require more complex programming than is needed for currently used aligners, where only the edge along the gum line needs to be trimmed. Alternatively, the entire apparatus can be 3-D printed and it is likely that is the way the industry will turn once non-toxic printable plastics become available.

The curved interconnecting elements can be a relatively flat, U-shaped ribbon made of plastic or metal, for example. However, FIGS. 13-21 illustrate that the physical properties of the curved interconnecting elements can be modified by the placement of reinforcing ribs or ridges 43, 44 to change the cross-section of the interconnecting elements 40. The ribs 43 strengthen the U-shaped loops and can change the torsional and flex properties of the loops. The ribs 44 can extend beyond the loops onto the bodies of the tooth-clasping elements 15 to increase the strength of the tooth-clasping elements, especially in the central areas of the clasps 15 where they engage the bonded attachments 12A, 12B. It is relatively easy to manufacture these strengthening ribs 43, 44 if the appliances are printed using a 3-D printer. In addition, the interconnecting elements are not necessarily flat, but rather could have any desired cross-sectional shape (e.g., circular, oval, tubular, a multi-strand cable, or a composite structure).

Figure 13:
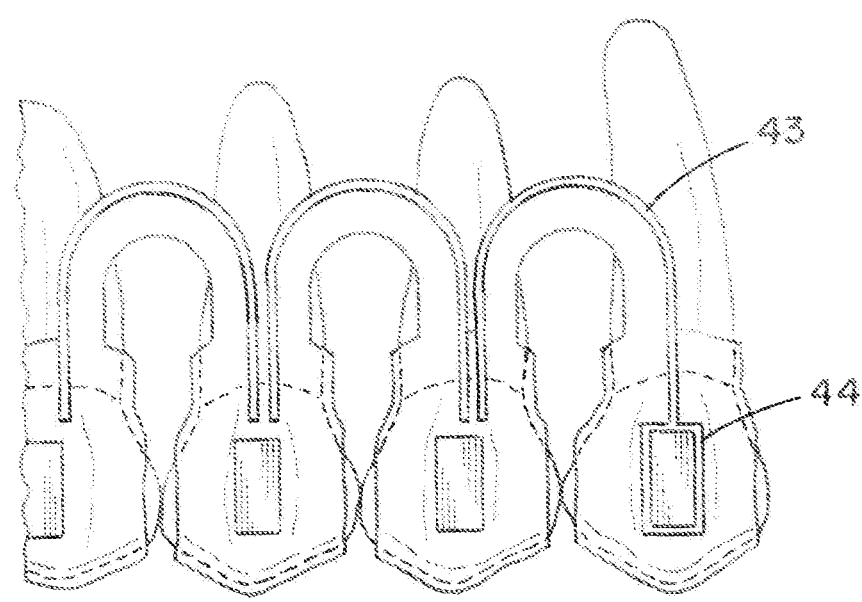
FIG. 13 presents an enlarged view of FIG. 12 with added support ridges 43 to the interconnecting elements and added support ridges 44 around the bonded attachments.

FIG. 13 is an enlargement of a portion of the appliance shown in FIG. 12. The outer edge of the flexible interconnecting elements include reinforcing ridges 43 that will be printed into the material forming the interconnecting elements. Note that the ridges 43 extend onto the flange section of the tooth-clasping elements and also onto the main tooth-contacting portion of the tooth-clasping elements. On one tooth, in this case the upper right canine tooth, the reinforcing ridge extends to and becomes continuous with a reinforcing ridge 44 that surrounds entirely the bonded attachment on the buccal surface of that tooth. The purpose of the reinforcing ridges is to add strength and to control the flex properties of both the tooth-clasping elements and the flexible interconnecting elements. It is to be understood that this disclosure does not limit the reinforcing ridges 43, 44 to this particular location or configuration. The reinforcing ridges can be located anywhere they are needed to add strength and to control the flex properties of the tooth-clasping elements and the flexible interconnecting elements.

Figure 17:
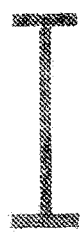
FIGS. 14-21 show cross-sectional views of interconnecting elements with a variety of shapes for the added support ridges 43, 44.
Figure 21:
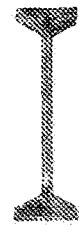
Figure 16:
Figure 20:
Figure 15:
Figure 19:
Figure 14:
Figure 18:
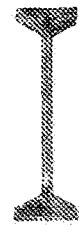

FIGS. 14-21 illustrate several possible configurations for reinforcing ridges that can be placed where they are needed on the flexible interconnecting elements or on tooth-clasping elements. These reinforcing ridges can be any suitable cross-sectional shape. FIG. 14 shows two rectangular projections to form a C-shape. FIG. 15 shows a single rectangular projection to form a T-shape. FIG. 16 shows double rectangular projections. FIG. 17 shows two rectangular projections to form an I-shape. FIG. 18 shows two tapered projections to form a C-shape. FIG. 19 shows a single tapered projection to form a T-shape. FIG. 20 shows double tapered projections. FIG. 21 shows double tapered projections on each side to form an I-shape.

The embodiment in FIG. 22 utilizes interconnecting elements 41 in an inverted U-shape. The inverted loop geometry may be better for keeping favorable forces applied to the teeth to minimize tooth tipping during space closure. Conversely, the tooth-clasping elements may be more difficult to place on the teeth if the loops are stretched open when the loops are inverted. In this embodiment, if produced by using vacuum-formed thin-shell plastic, the appliance can be fully fabricated with the loops in the normal configuration. After completion, the loops can be heated and flexed downward to assume their reverse configuration. This embodiment should become easily mass-producible using computer 3-D printing technology, and the inverted configuration should not require a separate step for loop flexion. The first embodiment shown in FIGS. 1-4 using wire interconnecting elements can also be manufactured with the wire loops in an inverted position, because a wire loop embodiment may be better suited for closing interdental spaces.

Returning to FIG. 22, this type of appliance can also be made from a thermoformed sheet by reheating the loops of the interconnecting elements 41 and flexing them downward into the inverted position. An electric heat gun with a blower, or an ultrasonic welder could be used to heat and re-form the thermoplastic material. If the appliance is printed, it can simply be printed in the inverted position. The appliance does not extend as deeply into the buccal vestibule, and therefore would not be as likely to cause irritation of the tissue of the cheek or gum tissue. It also conveys a mechanical advantage. If a loop is stretched open, such as when there is a space between teeth you are trying to close, there is not as much pressure placed to move the root apices closer together. If the loop is inverted, and the loop is stretched open, it tends to move the roots closer together. This same inverted loop geometry could be considered in the first embodiment, although you would not want to bend the wires downward. They should be mounted in the inverted position in the beginning.

Figure 23:
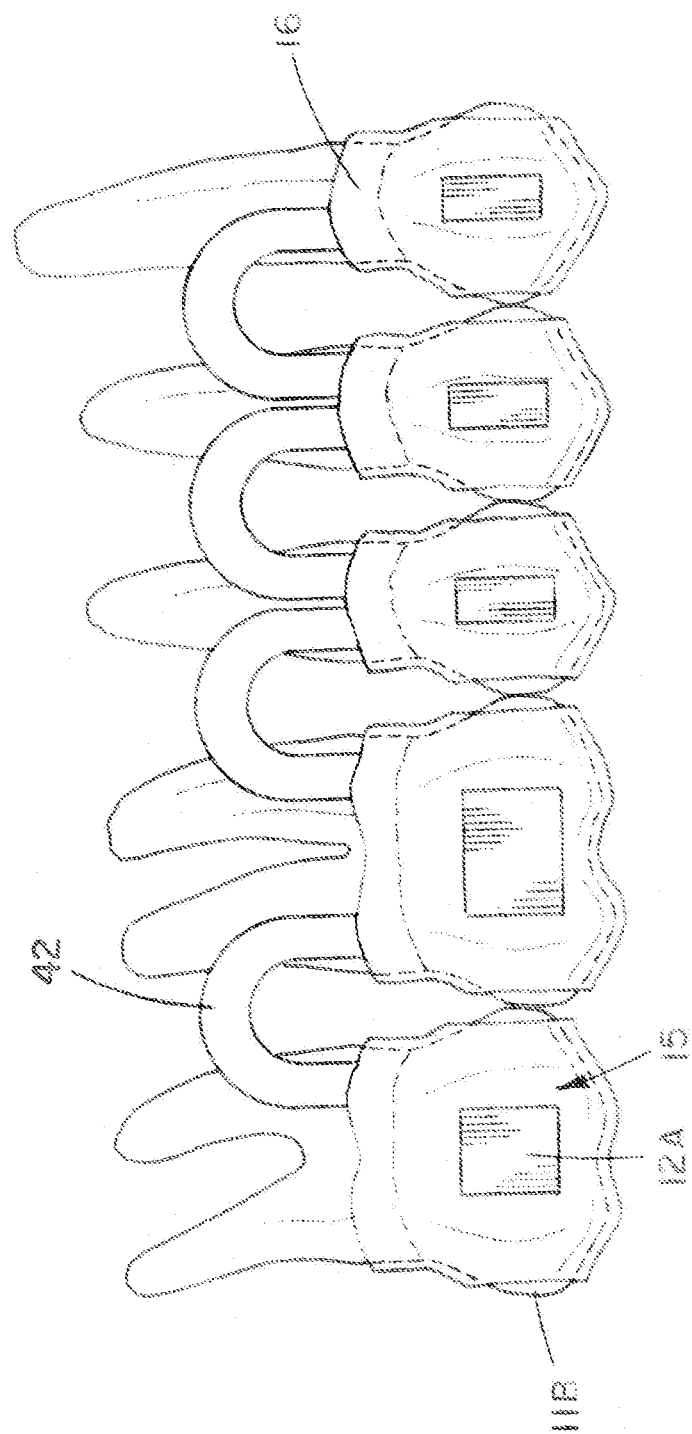
FIG. 23 is a modification of the embodiment shown in FIG. 12 in which different materials are used to fabricate the tooth-clasping elements 15 and the curved interconnecting elements 42.

The embodiment in FIG. 23 involves a modification of the materials utilized in forming positioner appliances and could be applied to any or all of the embodiments of the present invention disclosed herein. If a 3-D printer is utilized to manufacture a tooth-positioning appliance, we can take advantage of the current capabilities of some of the newer printers currently available. Multiple print nozzles can print more than one material with each pass of the printer over a given location. With this capability, we can print an appliance made entirely of one material, or we can print an appliance with blended or mixed materials, or we can print an appliance with some portions made of one material, and some portions made of another material. This capability will allow certain regions of the appliance to have greater or lesser flexibility, depending on the elastic modulus of the materials chosen for that particular region of the appliance. In the embodiment disclosed in FIG. 23, the tooth-clasping elements 15 are made of one material, while the curved interconnecting elements 42 are made of another material. The appliance will be printed as one monolithic whole, and the components will not need to be assembled or attached in a fabrication sequence. The printer will print one portion of the appliance and will go right on to print the other portion in a continuous motion as it is laying down the appliance layer by layer. The junction of the two materials can be a simple butt-joint junction where one material ends and another begins, or the junction can be a more complex intertwined zone with two materials interconnecting in such a way as to make the junction stronger, and more resistant to pulling apart. The two materials can have differing properties, such as elastic modulus, color, translucency, clarity, and strength such as yield strength, tensile strength, breaking strength, etc. The junction of the two materials may be stronger if the printer is programmed to mix or intertwine the materials in a brief junction zone.

The flexibility of the interconnecting elements can be varied depending on the type of malocclusion problem to be solved. In the early stages of treatment a very flexible interconnecting element material can be chosen to make it easier to engage a severely rotated tooth or a significantly tipped tooth. In later stages of treatment, the loops can be stiffer for better control over final tooth position just as the wire sizes are currently varied with the stage of treatment when fixed braces are used. The materials can also be chosen so that flexible materials are used for some interconnecting elements and stiffer interconnecting elements are used for other interconnecting elements.

In the embodiment shown in FIG. 12, the U-shaped interconnecting element 40 is made of the same clear material that forms the tooth-clasping elements 15. In other words, the appliance in FIG. 12 is a one-piece monolithic structure. In contrast, the appliance shown in FIG. 23 is preferably fabricated in one piece by using a 3-D printer that is capable of printing more than one material at a time. The tooth-clasping element 15 is preferably made of a clear material, and the interconnecting element 42 is preferably made of a different material, perhaps with a differing elastic modulus to control the flex properties of the curved loop. Because of the way the printer prints using multiple print nozzles, it is possible to gradually blend the materials into one another at the junction where the two materials join. It is unnecessary to attach the two portions.

Figure 24:
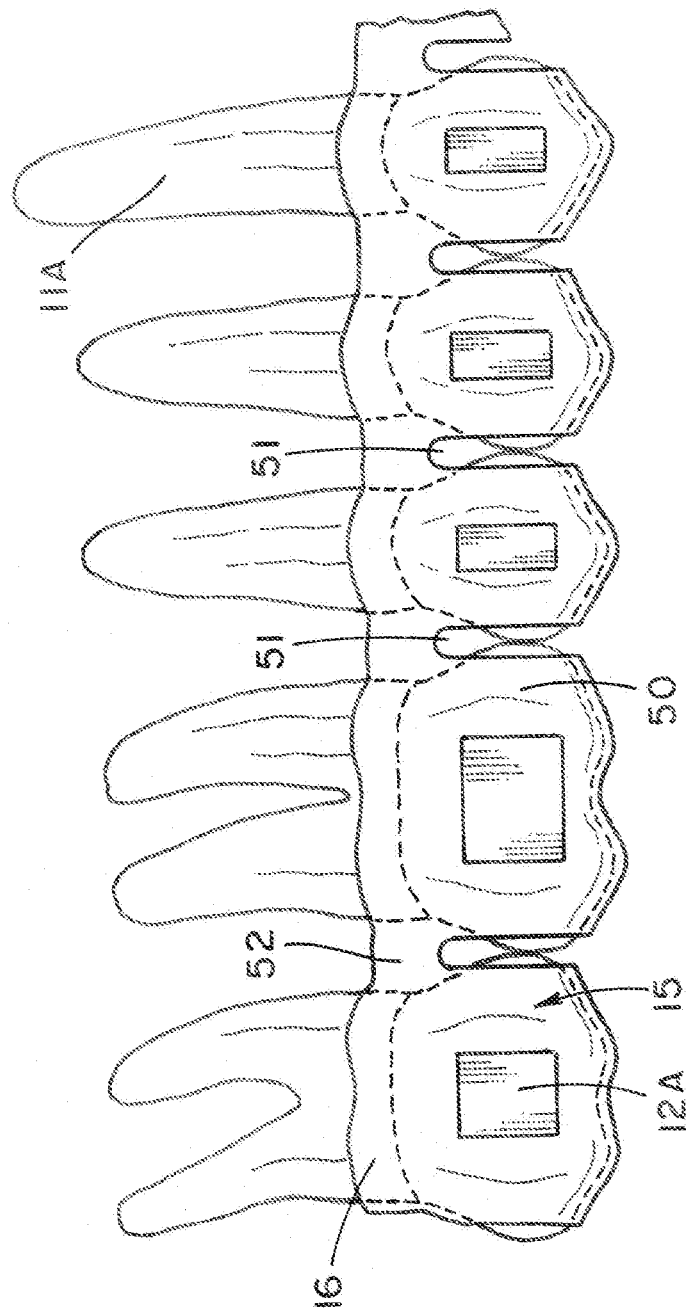
FIG. 24 shows a side view of another embodiment of the appliance fitted on some of the teeth in the upper right quadrant. This embodiment is also a single piece appliance like that shown in FIGS. 11 and 12. The difference is the flange portion 16 of the appliance covering some of the gum tissue on the facial side (shown) and lingual side (not shown) and the interdental portion 52 of the flange function as the flexible interconnecting elements.

The embodiment shown in FIG. 24 is formed of a single piece of material that is clear as it covers the anterior teeth. It can be manufactured by thermoforming a sheet of plastic material over a model of teeth, or it can be printed using a 3-D printer. There are no separately manufactured interconnecting elements as in the first embodiment. In its simplest embodiment, a single-piece tooth positioning appliance can be vacuum-formed over a plastic model. Flanges 16 of the appliance extend over the gum tissue. A difference in this embodiment is the flange 16 of the appliance also covers the interdental area including the interdental papillae, not just the gum tissue over the roots of the teeth as in the other embodiments of the present invention. Cuts are made between each tooth through the plastic shell material, but they do not entirely separate the shell into individual tooth-clasping elements. The cut-away area 51 between the teeth ends near the gum line in a small radius arch forming a U-shaped interconnecting element 52. The region of the appliance consisting of the flange portion of the appliance, including the flange area between the teeth covering the interdental papillae area adjacent to the interdental cuts 51 serves the same function as the interconnecting loop-shaped element 17 between two adjacent tooth-clasping elements in the earlier embodiments. Without the flange extension of the appliance over the gum tissue there would not be sufficient material to provide the needed flexibility for the interdental portion of this appliance to serve the function of the flexible interconnecting elements as shown in the third embodiment. If this appliance is printed using a 3-D printer, the same basic shape and size of the appliance as in the thermoformed version would be produced. Rather than making cuts in the material to produce the interdental voids, the printer would simply not print the areas where the thermoformed appliance is cut away.

Alternatively, the embodiment depicted in FIG. 24 can be fabricated by removing some of the appliance material to make the appliance more flexible. There are two ways this material can be considered to be "removed." First, if the appliance is made by thermoforming a sheet of material over a model, then a portion of that material can be removed by cutting it away using a CNC milling machine or a CNC laser cutter. Second, if the appliance is fabricated by a 3-D printer, then selected portions of the coverage of the plastic over the teeth will not be printed, leaving spaces where the coverage is chosen to be absent. The embodiment shown in FIG. 24 is much like the embodiment in FIGS. 11 and 12, in that both embodiments can be made of a single piece of material covering each dental arch. The flange material on the facial and lingual sides of the teeth covering the gum tissue area, and the additional flange material covering the interdental area, serves as the flexible interconnecting element. This additional flange material covering the interdental gum tissue area (specifically covering the interdental papillae) is shown only in FIG. 24 but it is to be understood that it could be present in any of the embodiments described herein if there is not a need for a separate tooth-clasping element for each tooth.

In some stages of treatment using an appliance system, one may use the embodiment from FIGS. 1-4 between two adjacent teeth, the embodiment from FIGS. 11-12 between the next two teeth, and possibly the embodiment from FIG. 24 between the next two teeth. In later stages of treatment, as the teeth become better aligned, there will be groups of teeth combined together into units where there are no interconnecting elements. This combining of the teeth into groups is shown in a separate related disclosure of a space closing appliance. In FIG. 24 there are no added curved loops to serve as the flexible interconnecting elements as in FIGS. 11 and 12. The flange material serves as a smaller loop or interconnecting element in FIG. 24. This embodiment is simpler and smaller than FIGS. 11 and 12, and could still be more effective for small movements than a conventional tooth positioning appliance as is now manufactured by several companies.

Figure 25:
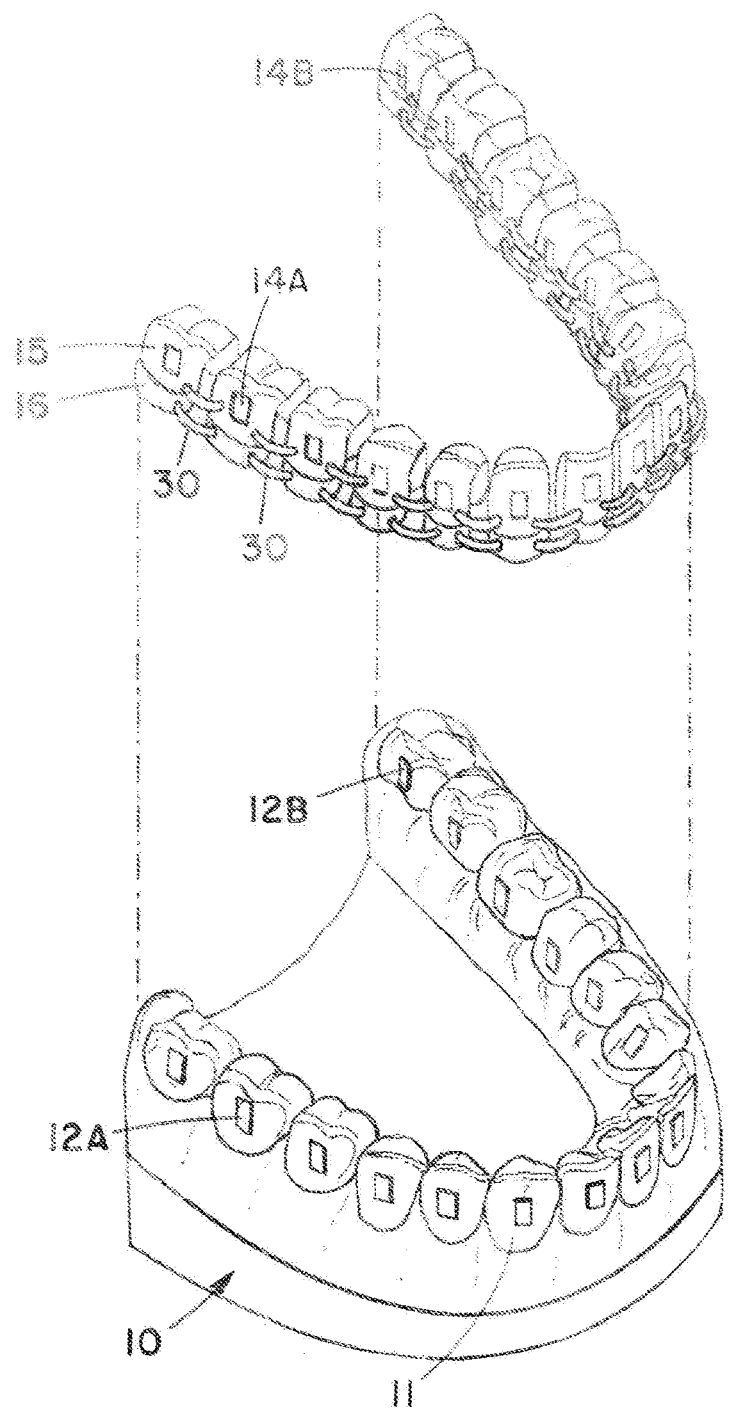
FIG. 25 shows a perspective view of a lower arch dental model with another embodiment of the appliance positioned above it. The small curved flexible polymer interconnecting elements are shown between the tooth-clasping elements. Dotted lines indicate the path the appliance would follow to be seated in place on the model.
Figure 26:
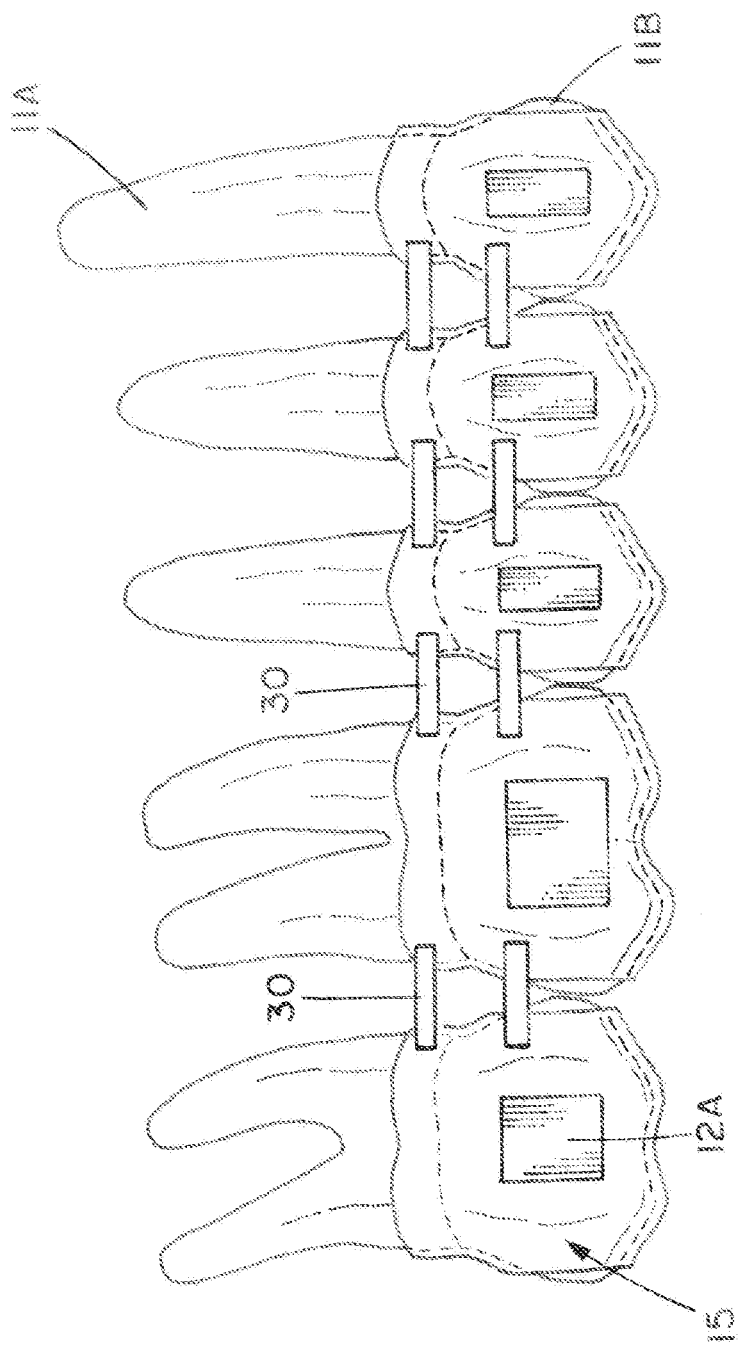
FIG. 26 shows a side view of the appliance fitted on some of the teeth in the upper right quadrant.
Figure 27:
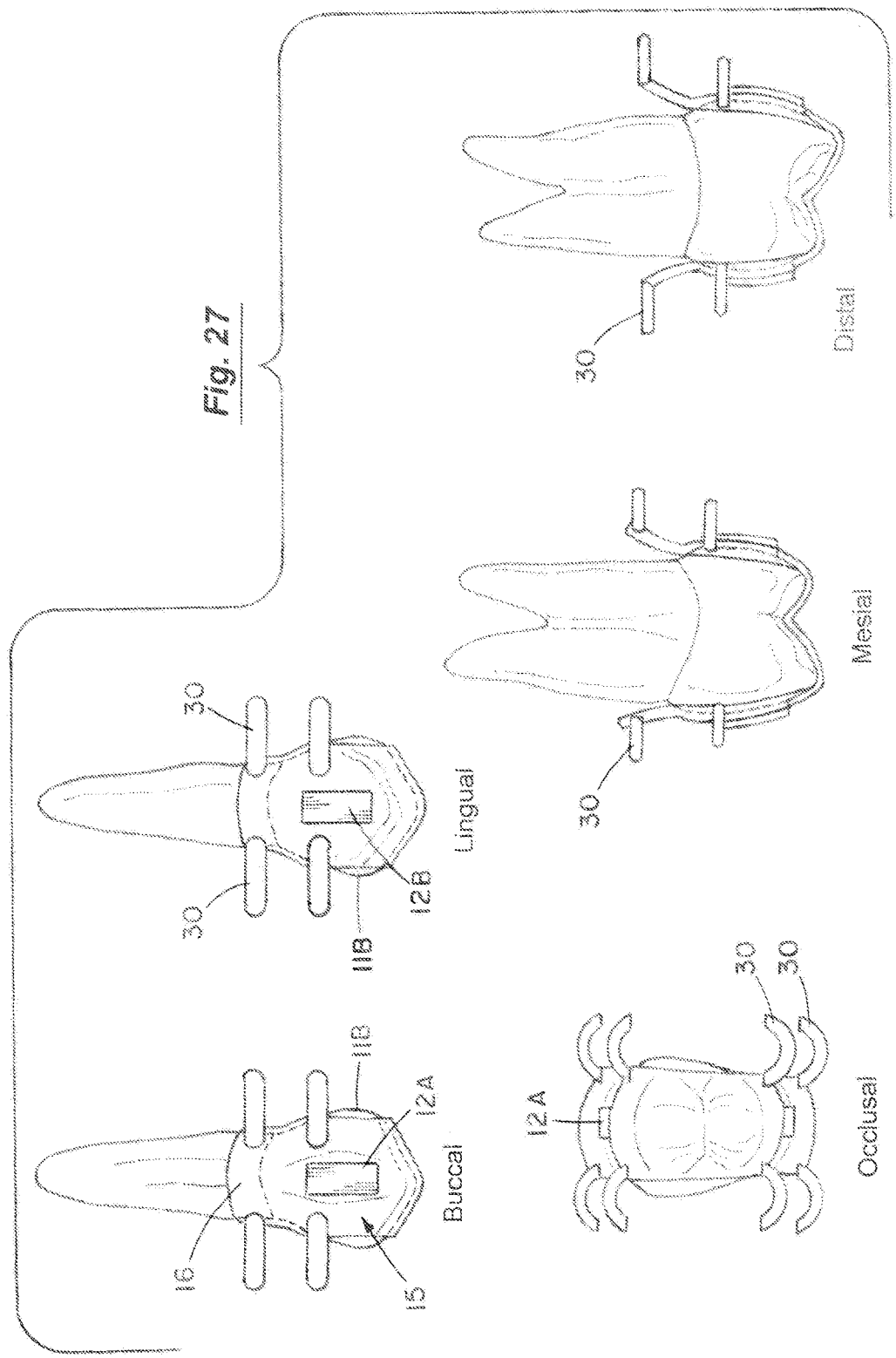
FIG. 27 shows views from five different directions of a single tooth (upper right first premolar) with bonded attachments 12A and 12B, a tooth-clasping element 15, and small, curved flexible interconnecting elements 30 in place.

FIGS. 25-27 show an embodiment having clear tooth-clasping elements 15 with interconnecting elements 30 that are U-shaped in horizontal planes extending outward from the tooth-clasping elements. In other words, each tooth-clasping element 15 is connected to the adjacent tooth-clasping element using short flexible U-shaped interconnecting elements 30 curving outward in horizontal planes, attached between the crown portion of the tooth-clasping elements and also between the flange section over the gum line. It should be noted that the curvature of the interconnecting elements 30 could be in more than one plane. The materials of the tooth-clasping elements 15 and the materials of the interconnecting elements 30 are preferably of differing materials, with the interconnecting elements 30 being more flexible. This embodiment could be easily printed, using a multiple nozzle 3D printer. The interconnecting elements 30 would be oriented in a flat horizontal plane with the outer portion of the curve directed away from the teeth (i.e., toward the cheek on the buccal side attachment and toward the tongue on the lingual side). Preferably, there are four interconnecting elements between each adjacent pair of tooth-clasping elements, one above the other on both the buccal and lingual sides of the teeth. However, any number of interconnecting elements could be used. It is anticipated that this embodiment would work well to correct minor rotations and crowding.

This embodiment may also offer the advantage of being less visible than the embodiments in FIGS. 1-4 and 11-12. For example, the interconnecting elements 30 can be made of any suitable flexible material including but not limited to: clear vinyl, clear silicone, and clear urethane, or some other material that is not clear. In the posterior teeth, they do not have to be clear because they will be seldom seen. If this positioner is fabricated by a 3-D digital printer, the flexible interconnecting elements can be printed simultaneously with the clear tooth-clasping portion.

Figure 28:
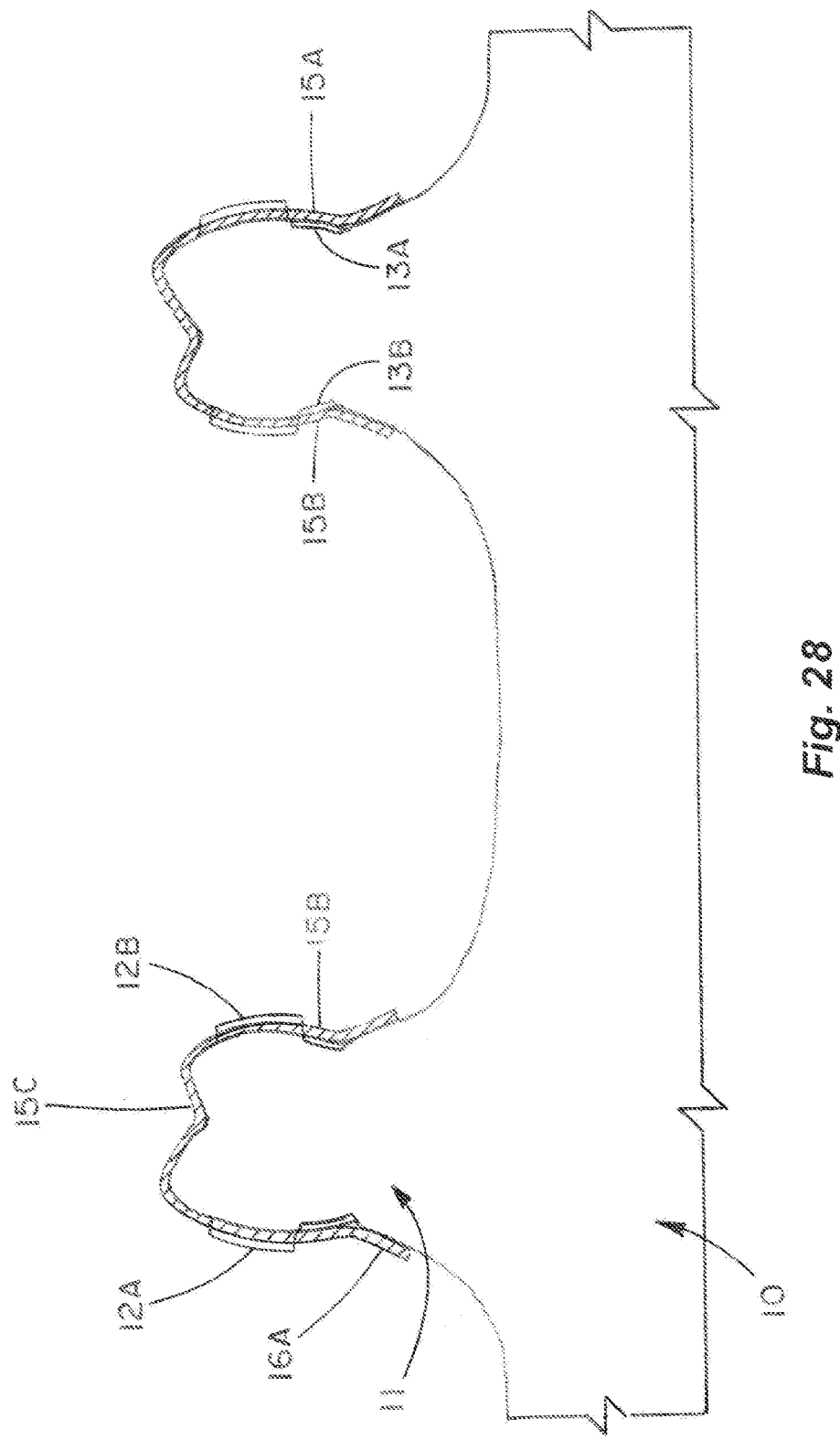
FIG. 28 is a cross-sectional view of a dental model 10 of the lower teeth with the plane passing transversely through the centers of the second premolar teeth 11. The tooth-clasping elements on the lower second premolar teeth are shown in place, seated on the teeth of the dental model. The external surfaces 13A and 13B of the teeth in the model, on both the buccal and lingual sides of the teeth, between the gum line and the bonded attachment have been moved inward (toward the center of the tooth) a small distance, as indicated by the dotted lines.
Figure 29:
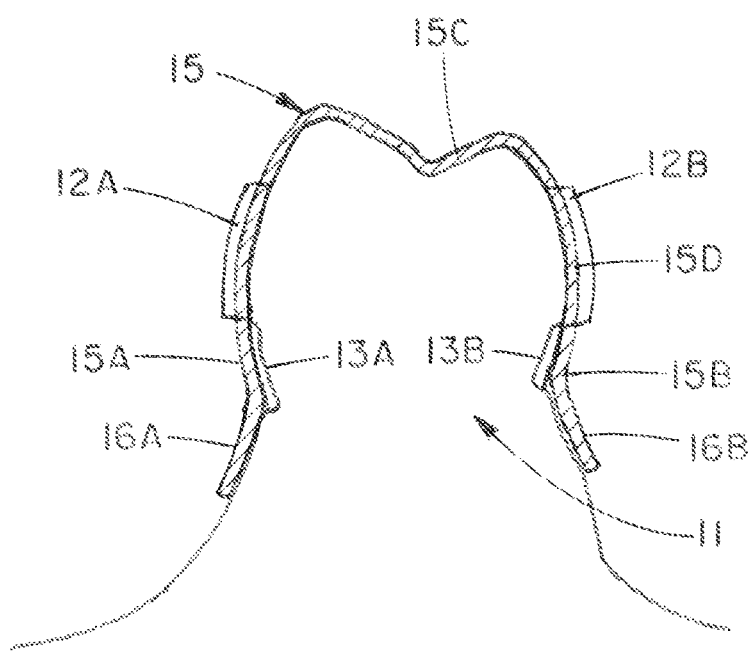
FIG. 29 is a detail cross-sectional view of the dental model with the tooth-clasping elements corresponding to FIG. 28.

FIGS. 28 and 29 show an embodiment of a tooth-clasping element 15 that is pre-loaded to more effectively engage a tooth. This modification could be applied to any or all of the previous embodiment disclosed herein. The digital data set corresponding to the shape of the dental model for any particular stage could be modified to move the labial and/or lingual surfaces 13A, 13B of the tooth, found between the level of the bonded attachment and the gum line, inward toward the center of the tooth by a small distance. Then, whether the appliance is printed, or if it is thermoformed over a digitally printed tooth model, the appliance will have a tighter fit along the gum line. Currently, thermoformed positioners have a tendency to become stretched after they have been worn for a few days. The material relaxes. The appliances become loose after they have been worn. The modification of the digital representation of the tooth surface prior to formation of the appliance will result in a tooth-clasping element that is pre-loaded when it fits over the full-sized natural tooth, resulting in a tighter fit of the appliance.

In particular, the area of the CAD model located between the bonded attachments and the gum line is modified in the digital file representing the 3-D surface contours of the model. The surfaces 13A and 13B representing the portions of the patient's tooth on both the buccal and lingual sides of the tooth from the gingival edge of the bonded attachment to the gum line are moved inward toward the center of the tooth by a distance representing about 1-25% of the thickness of the tooth. When a digital model is made of the tooth upon which to fabricate a thermoformed appliance, or when a 3-D printed appliance is fabricated which does not require the use of a 3D model under it for support for printing purposes, the corresponding modified surface contours 15A, 15B in the tooth-clasping element based with the aforementioned areas 13A, 13B of the model that were moved inward, will cause the fabricated appliance to have a pre-load so in these areas, resulting in a tighter fit in these areas. The gum line flange areas will not be affected by the change in the surface contours, but when the appliance is placed on the teeth, the real contour of the tooth will force the tooth-clasping element outward, and the gingival flange area will be forced outward slightly away from the gum tissue, providing a little more clearance to avoid having the flange region of the appliance impinge on the gum tissue.

Figure 30:
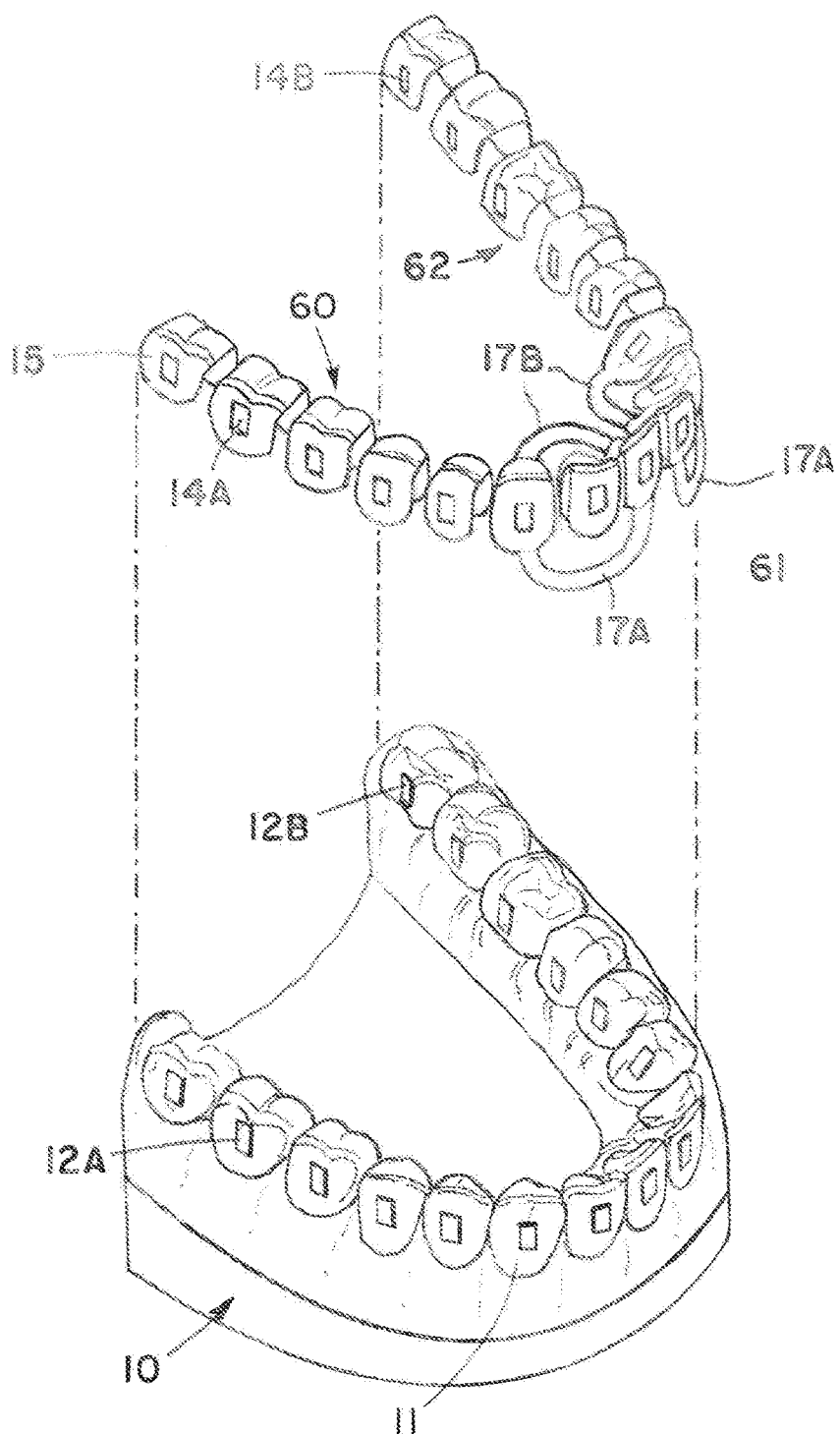
FIG. 30 is a perspective view of a lower dental arch 10 with another embodiment of an appliance having longer interconnecting elements 17A and 17B on both the buccal and lingual aspects of the appliance segments.
Figure 31:
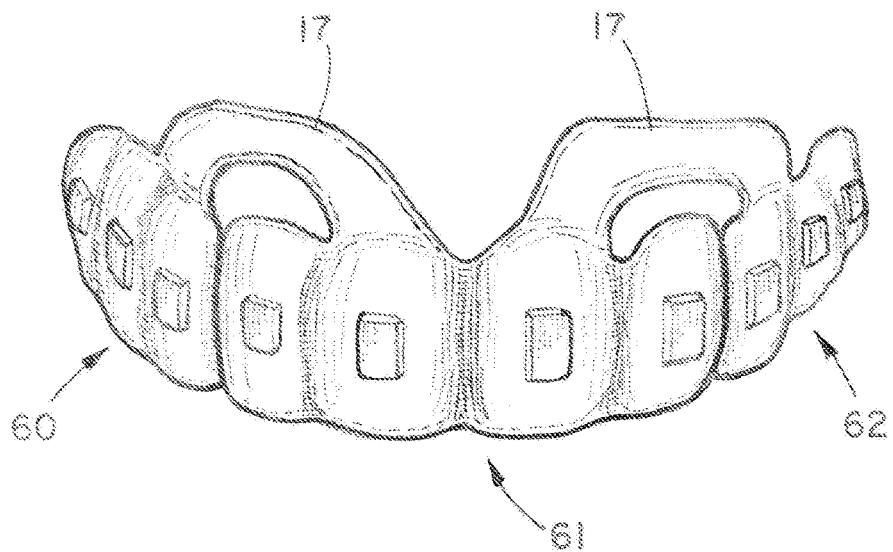
FIG. 31 is a front view of another embodiment of the appliance with longer interconnecting elements 17 on the buccal aspect of the appliance segments.
Figure 32:
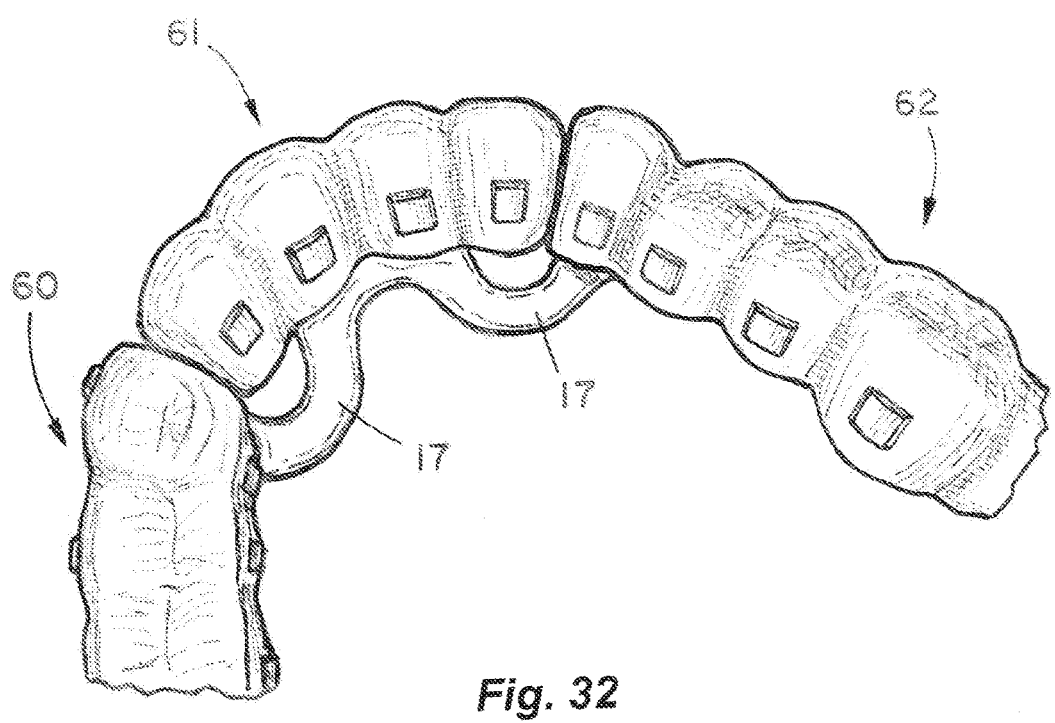
FIG. 32 is a bottom view corresponding to FIG. 31.

FIG. 30 illustrates another embodiment of the present invention having longer interconnecting elements 17A and 17B on both the buccal and lingual aspects. The interconnecting elements 17A, 17B extend between the appliance segments 60-62 and skip over one or more teeth. FIGS. 31 and 32 show another embodiment of the appliance with longer interconnecting elements 17 on only the buccal aspect of the appliance segments.

These embodiments can be used, for example, in cases where we are trying to intrude incisors. Here, the interconnecting elements 17A, 17B extend from the canine over to the central incisor, skipping the lateral incisor. All four incisors are held together as a unit by a single appliance segment 61, and the remaining teeth on either side of the incisors are held together by two appliance segments 60 and 62. These embodiments are primarily intended to overcome the problem during intrusion where most of the intrusive force is placed on the lateral incisor, and the intrusion force is dissipated somewhat by the time it is transferred to the larger central incisor, which is a larger tooth and requires more force to intrude it.

Figure 33:
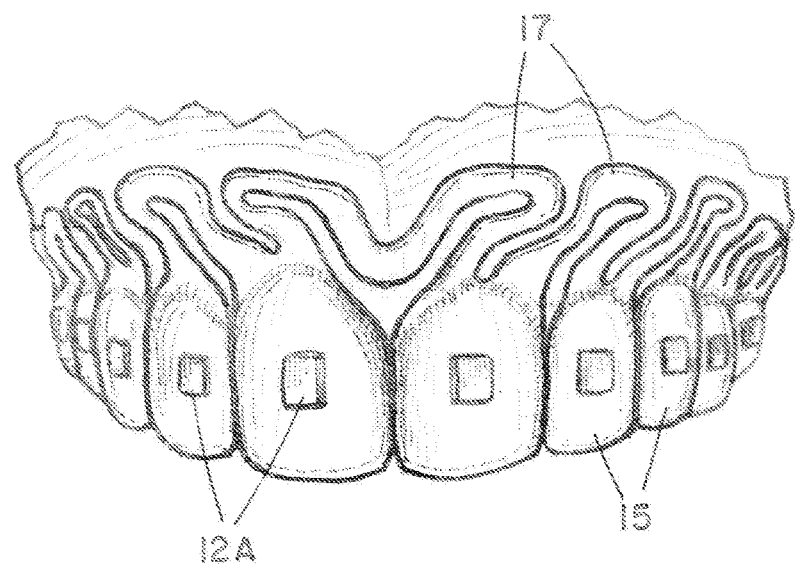
FIG. 33 is a front view of yet another embodiment of an appliance having longer interconnecting elements 17 between the tooth-clasping elements 15 on individual teeth.
Figure 34:
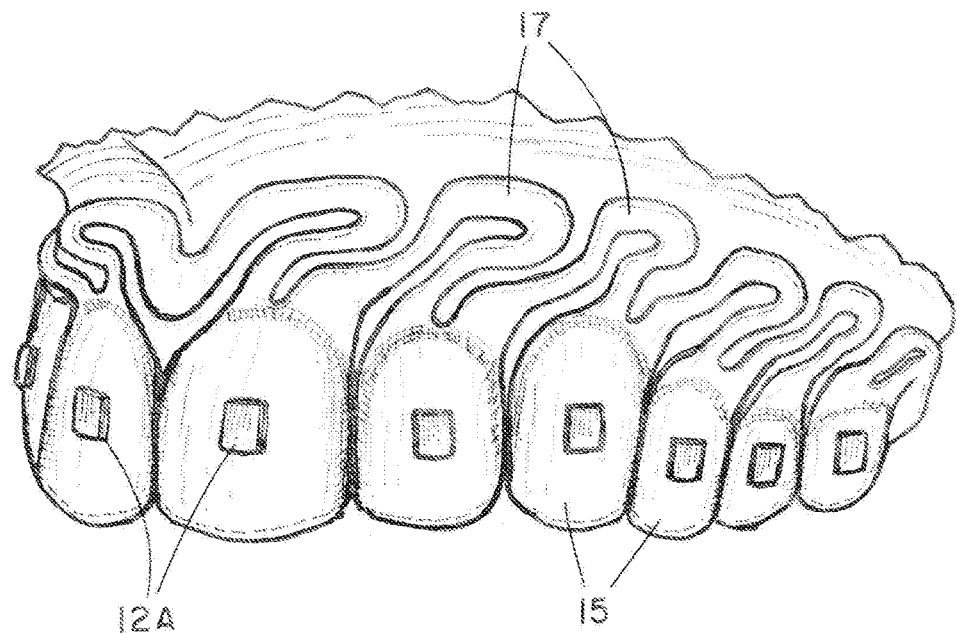
FIG. 34 is a side view corresponding to FIG. 33.

FIGS. 33 and 34 show yet another embodiment of the present invention having longer interconnecting elements 17 between the tooth-clasping elements 15 on individual teeth. These interconnecting elements 17 have a more elongated, irregular shape that allow a greater range of relative motion between the tooth-clasping elements 15 and their respective teeth. In addition, the physical properties of interconnecting elements 17 can be individually designed based on their dimensions, shapes and material properties.

Figure 35:
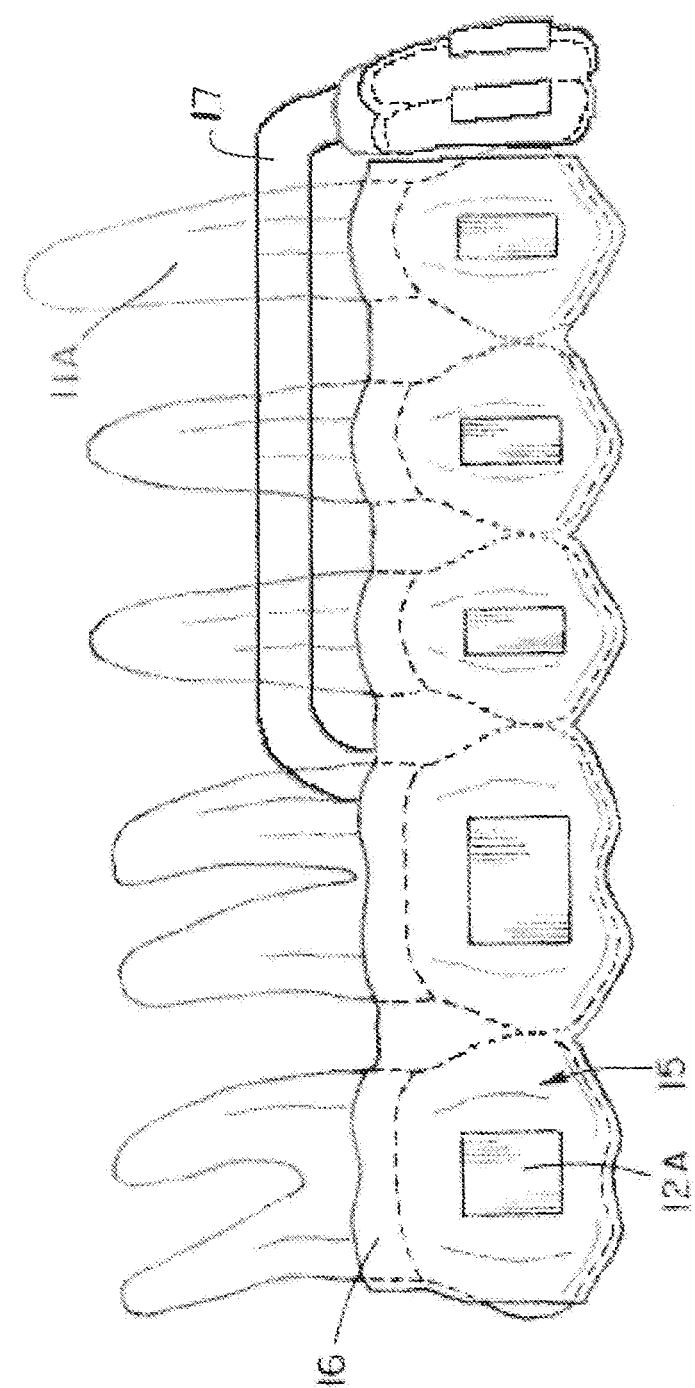
FIG. 35 is a right side view of another embodiment of an appliance on the upper right teeth with an interconnecting element 17 connected from the posterior appliance segment near the first molar tooth to the anterior appliance segment directly above the central incisors.

FIG. 35 shows the posterior teeth all connected into one tooth clasping element, extending from the second molar to the cuspid. A flexible clear plastic interconnecting element 17, (there is one on each side with only the right side shown in this figure) in this case made of the same continuous piece of plastic that forms the rest of the appliance, extends forward and drops down directly above the central incisor to engage a four-unit anterior tooth clasping element that envelopes the incisors, in much the same manner as was shown in FIGS. 33 and 34. The appliance is activated so that vertical force is directed straight up at the central incisors.

Figure 36:
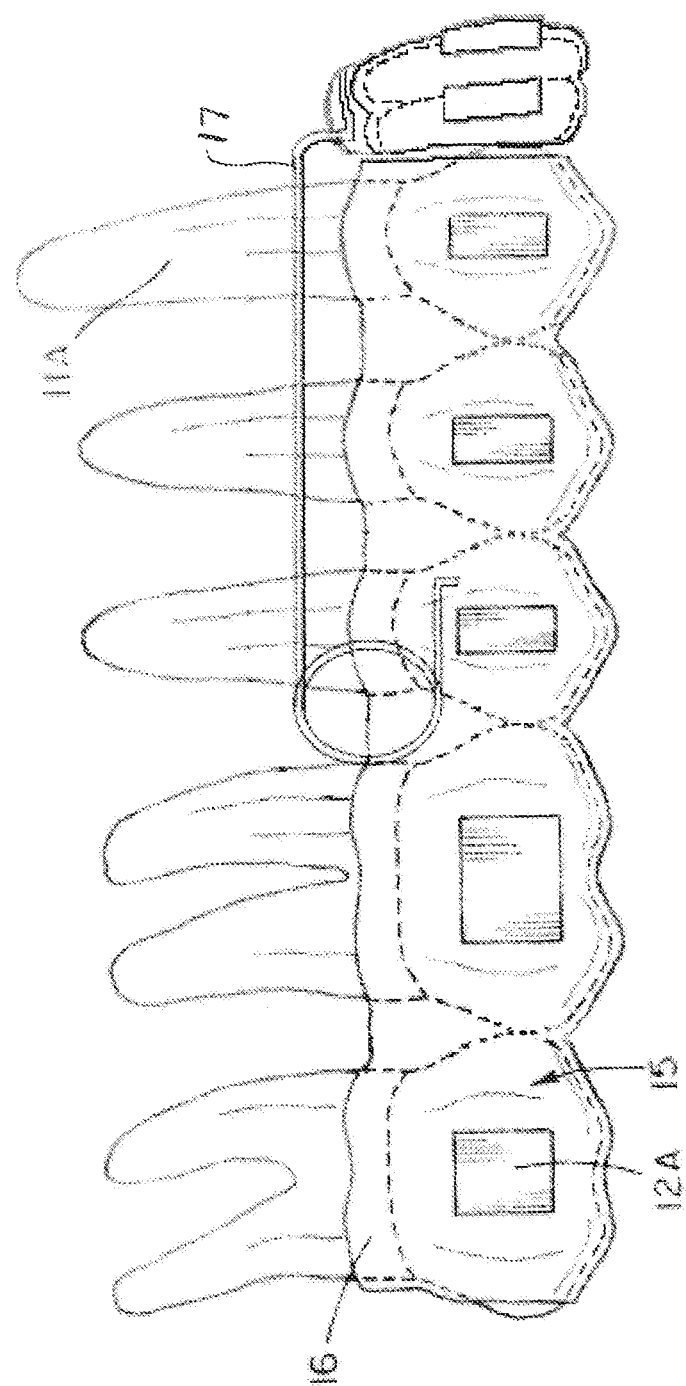
FIG. 36 is a right side view of another embodiment of an appliance on the upper right teeth with an interconnecting element 17 made of wire connecting the posterior appliance segment with the anterior appliance segment.

FIG. 36 shows a similar appliance to FIG. 35, but in this case the active interconnecting element 17 is made of wire connected to the posterior tooth clasping element. The means of attachment is not shown, but could include all of the methods discussed earlier for attaching wires. The wire has a helical coil near to where it attaches to the posterior tooth clasping element, and the anterior end of the wire extends forward to the four-unit tooth clasping element surrounding the incisor teeth. It is anticipated that the wire will be attached to the four-unit anterior tooth clasping element in the flange area covering the gum tissue above the crowns of the teeth where it will be less visible under the upper lip. Preferably, the wire will be attached and will extend all the way across above the four incisor teeth to the left side of the mouth where it will be a mirror image of the wire on the right side and will be the active arm on the left side, also containing a helical coil before it is attached to the posterior tooth clasping element on the left side. The left and right side posterior tooth clasping elements will likely be attached together across the palate by any suitable rigid means including clear plastic. The left and right posterior segments can also be attached to each other across the palate using a plastic or metal trans-palatal arch or bar.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

We claim:

1. A tooth-positioning appliance removably securable to a patient's teeth, said appliance comprising:
   bonded attachments adapted to be bonded to protrude from selected teeth;
   a plurality of tooth-clasping elements removably engaging the bonded attachments to attach the appliance to selected teeth, wherein at least one tooth-clasping element includes a thin shell with a recess for receiving at least one tooth and extending from the lingual aspect, over the occlusal aspect and to the labial aspect of at least one tooth with opposing lateral edges; and
   a flexible curved interconnecting element extending between a series of the tooth-clasping elements and having curved segments between adjacent tooth-clasping elements.

2. The tooth-positioning appliance of claim 1 wherein the curved interconnecting element extends between the lateral edges of adjacent tooth-clasping elements.

3. The tooth-positioning appliance of claim 1 wherein the curved interconnecting element is adapted to extend adjacent to the patient's gingiva between the tooth-clasping elements.

4. The tooth-positioning appliance of claim 1 wherein the interconnecting element curves toward the patient's gingiva between tooth-clasping elements.

5. The tooth-positioning appliance of claim 1 wherein the tooth-clasping elements and curved interconnecting element are fabricated as a single piece.

6. The tooth-positioning appliance of claim 1 wherein the tooth-clasping element further comprises a recess for receiving and engaging a bonded attachment protruding from a tooth.

7. The tooth-positioning appliance of claim 1 wherein the curved interconnecting member comprises a wire having curved segments between adjacent tooth-clasping elements.

8. The tooth-positioning appliance of claim 1 wherein at least one of said tooth-clasping elements further comprises a flange adapted to extend over the gum tissue of a patient.

9. The tooth-positioning appliance of claim 1 wherein the curved interconnecting member comprises a U-shaped ribbon.

10. The tooth-positioning appliance of claim 9 wherein the curved interconnecting member further comprises a reinforcing rib.

11. The tooth-positioning appliance of claim 1 wherein the curved interconnecting member further comprises a helical coil.

12. A tooth-positioning appliance removably securable to a patient's teeth, said appliance comprising:
    attachments adapted to be bonded to protrude from selected teeth;
    a plurality of thin-shelled appliance segments, each having recesses for removably engaging a group of teeth and extending from the lingual aspect, over the occlusal aspect and to the labial aspect of the teeth with opposing lateral edges; and having tooth-clasping elements for removably engaging attachments on selected teeth in said group, to thereby attach the appliance segments to the selected teeth; and
    a flexible curved interconnecting element extending between a plurality of appliance segments with curved segments extending between adjacent appliance segments.

13. The tooth-positioning appliance of claim 12 wherein the curved interconnecting element extends adjacent to a patient's gingiva between the tooth-clasping elements.

14. The tooth-positioning appliance of claim 12 wherein the curved interconnecting member comprises a wire having curved segments between adjacent tooth-clasping elements.

15. The tooth-positioning appliance of claim 12 wherein the curved interconnecting element curves toward a patient's gingiva between tooth-clasping elements.

16. The tooth-positioning appliance of claim 12 wherein at least one of said tooth-clasping elements further comprises a flange adapted to extend over the gum tissue of a patient.

17. A tooth-positioning appliance removably securable to a patient's teeth, said appliance comprising:
- attachments adapted to be bonded to protrude from selected teeth;
- a plurality of tooth-clasping elements each having a thin shell removably engaging the bonded attachments to attach the appliance to selected teeth; each thin shell adapted to extend from the lingual aspect, over the occlusal aspect and to the labial aspect of at least one tooth with opposing lateral edges; and
- a flexible curved interconnecting element extending between a plurality of tooth-clasping elements and having curved segments extending between the lateral edges of the tooth-clasping elements adapted to be adjacent to a patient's gingiva.

18. The tooth-positioning appliance of claim 17 wherein the curved interconnecting member comprises a wire having curved segments between adjacent tooth-clasping elements.

19. The tooth-positioning appliance of claim 17 wherein at least one of the tooth-clasping elements further comprises a flange extending over the gum tissue of a patient.

20. The tooth-positioning appliance of claim 17 wherein the curved segments of the interconnecting element are substantially U-shaped.

\* \* \* \* \*